US008524679B2

(12) United States Patent
Pachuk

(10) Patent No.: US 8,524,679 B2
(45) Date of Patent: Sep. 3, 2013

(54) IN VIVO DELIVERY OF DOUBLE STRANDED RNA TO A TARGET CELL

(75) Inventor: Catherine Pachuk, Northborough, MA (US)

(73) Assignee: Veritas Bio, LLC, Plymouth Meeting, PA (US)

(*) Notice: Subject to any disclaimer, the term of this patent is extended or adjusted under 35 U.S.C. 154(b) by 609 days.

(21) Appl. No.: 12/514,237

(22) PCT Filed: Nov. 6, 2007

(86) PCT No.: PCT/US2007/083805
§ 371 (c)(1),
(2), (4) Date: Sep. 2, 2010

(87) PCT Pub. No.: WO2008/118212
PCT Pub. Date: Oct. 2, 2008

(65) Prior Publication Data
US 2010/0323001 A1 Dec. 23, 2010

Related U.S. Application Data

(60) Provisional application No. 60/857,501, filed on Nov. 8, 2006, provisional application No. 60/907,014, filed on Mar. 16, 2007, provisional application No. 60/956,610, filed on Aug. 17, 2007, provisional application No. 60/974,695, filed on Sep. 24, 2007, provisional application No. 60/978,950, filed on Oct. 10, 2007.

(51) Int. Cl.
C12N 15/11 (2006.01)
A61K 48/00 (2006.01)
C07H 21/02 (2006.01)
C07H 21/04 (2006.01)

(52) U.S. Cl.
USPC .................................. 514/44 A; 536/24.5

(58) Field of Classification Search
USPC .......................................... 514/44; 536/24.5
See application file for complete search history.

(56) References Cited

U.S. PATENT DOCUMENTS

| 5,580,859 A | 12/1996 | Felgner et al. |
| 5,589,466 A | 12/1996 | Felgner et al. |
| 5,624,802 A | 4/1997 | Urdea et al. |
| 5,650,096 A | 7/1997 | Harris et al. |
| 5,783,565 A | 7/1998 | Lee et al. |
| 5,830,877 A | 11/1998 | Carson et al. |

(Continued)

FOREIGN PATENT DOCUMENTS

| WO | WO 00/63364 | 10/2000 |
| WO | WO 2004/011624 A2 | 2/2004 |

(Continued)

OTHER PUBLICATIONS

Abbott et al., *Evidence that the 14 kDa soluble β-galactoside-binding lectin in man is encoded by a single gene*, Biochem J., 259:291-294 (1989).

(Continued)

Primary Examiner — Terra Cotta Gibbs
(74) Attorney, Agent, or Firm — RatnerPrestia

(57) ABSTRACT

The invention encompasses methods of delivering nucleic acids, including dsRNA, to mammalian target cells in vivo via intercellular transfer, wherein the dsRNA is delivered to or expressed in a first cell different from the target cell, wherein the first cell facilitates delivery of the dsRNA to the target cell.

17 Claims, 11 Drawing Sheets

(56) References Cited

U.S. PATENT DOCUMENTS

| | | | |
|---|---|---|---|
| 5,837,533 | A | 11/1998 | Boutin |
| 5,993,434 | A | 11/1999 | Dev et al. |
| 6,127,170 | A | 10/2000 | Boutin |
| 6,181,964 | B1 | 1/2001 | Hofmann et al. |
| 6,217,900 | B1 | 4/2001 | Ciccarelli et al. |
| 6,233,482 | B1 | 5/2001 | Hofmann et al. |
| 6,241,701 | B1 | 6/2001 | Hofmann |
| 6,379,965 | B1 | 4/2002 | Boutin |
| 6,379,966 | B2 | 4/2002 | Monahan et al. |
| 6,383,512 | B1 | 5/2002 | Ciccarelli et al. |
| 6,413,942 | B1 | 7/2002 | Felgner et al. |
| 6,506,559 | B1 | 1/2003 | Fire et al. |
| 6,516,223 | B2 | 2/2003 | Hofmann |
| 6,567,694 | B2 | 5/2003 | Hayakawa |
| 6,678,556 | B1 | 1/2004 | Nolan et al. |
| 6,723,077 | B2 | 4/2004 | Pickup et al. |
| 7,148,205 | B2 | 12/2006 | Monahan et al. |
| 7,171,264 | B1 | 1/2007 | Hofmann et al. |
| 7,173,116 | B2 | 2/2007 | Fewell et al. |
| 2004/0014645 | A1 | 1/2004 | Draghia-Akli et al. |
| 2004/0059285 | A1 | 3/2004 | Mathiesen et al. |
| 2004/0092907 | A1 | 5/2004 | Mathiesen et al. |
| 2004/0152117 | A1 | 8/2004 | Giordano et al. |
| 2004/0259828 | A1 | 12/2004 | Wolff et al. |
| 2005/0042272 | A1 | 2/2005 | Hou et al. |
| 2005/0052630 | A1 | 3/2005 | Smith et al. |
| 2005/0070841 | A1 | 3/2005 | Mathiesen et al. |
| 2005/0130184 | A1 | 6/2005 | Xu et al. |
| 2005/0130919 | A1 | 6/2005 | Xu et al. |
| 2006/0084617 | A1 | 4/2006 | Satishchandran |
| 2006/0099622 | A1 | 5/2006 | Ni et al. |
| 2006/0135456 | A1 | 6/2006 | Hannon et al. |
| 2006/0183196 | A1 | 8/2006 | Chen et al. |
| 2006/0263764 | A1 | 11/2006 | Pachuk |
| 2007/0128708 | A1 | 6/2007 | Gamelin |
| 2007/0244067 | A1 | 10/2007 | Budker et al. |

FOREIGN PATENT DOCUMENTS

| | | | |
|---|---|---|---|
| WO | WO 2004/035765 | A2 | 4/2004 |
| WO | WO 2004/035766 | A2 | 4/2004 |
| WO | WO 2004/076629 | A2 | 9/2004 |
| WO | WO 2005/059111 | A2 | 6/2005 |
| WO | WO 2006/033756 | A2 | 3/2006 |
| WO | WO 2008/147430 | A2 | 12/2008 |

OTHER PUBLICATIONS

Aigner, *Delivery System for the Direct Application of siRNAs to Induce RNA Interference (RNAi) In Vivo*, Journal of Biomedicine and Biotechnology, pp. 1-15 (2006).
Aumüller et al., *Apocrine secretion—fact or artifact?*, Ann. Anat. vol. 181 (1999) Abstract.
Chen et al., *Real-time quantification of microRNAs by stem-loop RT-PCR*, Nucleic Acids Research, 33:1-9 (2005).
Chiu et al., *siRNA function in RNAi: A chemical modification analysis*, RNA, 9:1034-1048 (2003).
Cooper et al., *Evidence for Export of a Muscle Lectin from Cytosol to Extracellular Matrix and for a Novel Secretory Mechanism*, The Journal of Cell Biology, 110:1681-1691 (1990).
Cooper, *Galectin-1: Secretion and Modulation of Cell Interactions with Laminin*, Trends in Glycoscience and Glycotechnology, 9:57-67 (1997).
Couraud et al., *Molecular Cloning, Characterization, and Expression of a Human 14-kDa Lectin\**, The Journal of Biological Chemistry, 264:1310-1316 (1989).
Cronin et al., *The lac operator-repressor system is functional in the mouse*, Genes & Development, 15:1506-1517 (2001).
Alvarez-Erviti et al., *Delivery of siRNA to the mouse brain by systemic injection of targeted exosomes*, Nature Biotechnology, 29:341-347 (2011).
Giladi et al., *Small Interfering RNA Inhibits Hepatitis B Virus Replication in Mice*, Molecular Therapy, 8:769-776 (2003).

Hagstrom et al., *A Facile Nonviral Method for Delivering Genes and siRNAs to Skeletal Muscle of Mammalian Limbs*, Molecular Therapy, 10:386-398 (2004).
Hamar et al., *Small interfering RNA targeting Fas protects mice against renal ischemia-reperfusion injury*, PNAS, 101:14883-14888 (2004).
Harrison et al., *The 14 kDa β-galactoside binding lectin in myoblast and myotube cultures: localization by confocal microscopy*, Journal of Cell Science, 101:635-646 (1992).
Van Den Haute et al., *Lentiviral Vector-Mediated Delivery of Short Hairpin RNA Results in Persistent Knockdown of Gene Expression in Mouse Brain*, Human Gene Therapy, 14:1799-1807 (2003).
Herweijer et al., *Gene therapy progress and prospects: Hydrodynamic gene delivery*, Gene Therapy, 14:99-107 (2007).
Hirabayashi et al., *Complete Amino Acid Sequence of a β-Galactoside-Binding Lectin from Human Placenta*, J. Biochem. (Tokyo) 104:1-4 (1988).
Ibricevic et al., *Influenza Virus Receptor Specificity and Cell Tropism in Mouse and Human Airway Epithelial Cells*, Journal of Virology, 80:7469-7480 (2006).
Inagaki et al., *Oxidized galectin-1 promotes axonal regeneration in peripheral nerves but does not possess lectin properties*, Eur. J. Biochem., 267:2955-2964 (2000).
Baj-Krzyworzeka et al., *Tumour-derived microvesicles carry several surface determinants and mRNA of tumour cells and transfer some of these determinants to monocytes*, Cancer Immunol Immunother, 55:808-818 (2006).
Jauregui et al., *A quantitative analysis of lectin binding to adult rat hepatocyte cell surfaces*, In Vitro Cellular & Developmental Biology, 24:401-412 (1988).
Khlebnikov et al., *Regulatable Arabinose-Inducible Gene Expression System with Consistent Control in All Cells of a Culture*, Journal of Bacteriology, 182:7029-7034 (2000).
Khoury et al., *Efficient New Cationic Liposome Formulation for Systemic Delivery of Small Interfering RNA Silencing Tumor Necrosis Factor α in Experimental Arthritis*, Arthritis & Rheumatism, 54:1867-1877 (2006).
Krześlak et al., *Galectin-3 as a Multifunctional Protein*, Cell. Mol. Biol. Lett., 9:305-328 (2004).
Lamartina et al., *Stringent Control of Gene Expression In Vivo by Using Novel Doxycycline-Dependent Trans-Activators*, Hum Gene Ther., 13(2):199-210 (2002).
Landen et al., *Intraperitoneal Delivery of Liposomal siRNA for Therapy of Advanced Ovarian Cancer*, Cancer Biology & Therapy, 5:1708-1713 (2006).
Lewis, et al., *Systemic siRNA delivery via hydrodynamic intravascular injection*, Advanced Drug Delivery Reviews, vol. 59 (2007) Abstract.
McCaffrey et al., *Inhibition of hepatitis B virus in mice by RNA interference*, Nature Biotechnology, 21(6):639-44 (2003).
McCaffrey et al., *In Vivo Pre-Clinical Studies for RNA Interference Dcirected Therapies for Human Viral Hepatitis Infection*, Abstract No. 039, Keystone Symposia on siRNAs and miRNAs, (Apr. 18, 2004).
Mehul et al., *Plasma membrane targetting, vesicular budding and release of galectin 3 from the cytoplasm of mammalian cells during secretion*, Journal of Cell Science, 110:1169-1178 (1997).
Mittelbrunn et al., *Unidirectional transfer of microRNA-loaded exosomes from T cells to antigen-presenting cells*, Nature Communications, 2:1-10 (2011).
Morrissey et al., *Activity of Stabilized Short Interfering RNA in a Mouse Model of Hepatitis B Virus Replication*, Hepatology, 1349-1356 (2005).
Nagaoka, *Participation of a galectin-dependent mechanism in the hepatic clearance of tissue-type plasminogen activator and plasma kallikrein*, Thromb Res, 108:257-262 (2003).
Nickel, *Unconventional Secretory Routes: Direct Protein Export Across the Plasma Membrane of Mammalian Cells*, Traffic, 6:607-614 (2005).
Pachuk et al., *Characterization of a new class of DNA delivery complexes formed by the local anesthetic bupivacaine*, Biochimica et Biophysica Acta, pp. 20-30 (2000).

Park et al., *The asialoglycoprotein receptor clears glycoconjugates terminating with sialic acidα2,6GalNAc*, PNAS, 102:17125-17129 (2005).

Prud'Homme et al., *Electroporation-Enhanced Nonviral Gene Transfer for the Prevention or Treatment of Immunological, Endocrine and Neoplastic Diseases*, Current Gene Therapy, 6:243-273 (2006).

Ratajczak et al., *Embryonic stem cell-derived microvesicles reprogram hematopoietic progenitors: evidence for horizontal transfer of mRNA and protein delivery*, Nature Publishing Group, 20:847-856 (2006).

Rendahl et al., *Tightly Regulated Long-Term Erythropoietin Expression In Vivo Using Tet-Inducible Recombinant Adeno-Associated Viral Vectors*, Hum Gene Ther., 13(2):335-42, (2002).

Romano et al., *RNA interference-mediated prevention and therapy for hepatocellular carcinoma*, Oncogene, 25:3857-3865 (2006).

Seelenmeyer et al., *Cell surface counter receptors are essential components of the unconventional export machinery of galectin-1*, The Journal of Cell Biology, 171:373-381 (2005).

Song et al., *RNA interference targeting Fas protects mice from fulminant hepatitis*, Nature Medicine, 9(3):347-351 (2003).

Soutschek et al., *Therapeutic silencing of an endogenous gene by systemic administration of modified siRNAs*, Nature, 432(7014):173-178 (2004).

Thomas et al., *Tissue distribution of liposome-mediated epidermal growth factor receptor antisense gene therapy*, Cancer Gene Therapy, 10:518-528 (2003).

Valadi et al., *Exosome-mediated transfer of mRNAs and microRNAs is a novel mechanism of genetic exchange between cells*, Nature Cell Biology, 9:654-659 with supplementary information (64 pgs) (2007).

Wang et al., *Development of gene-switch transgenic mice that inducibly express transforming growth factor β1 in the epidermis*, Proc. Natl. Acad. Sci. USA, 96:8483-8488 (1999).

International Search Report PCT/US07/83805 dated Nov. 18, 2008.

International Search Report EP 07 87 3598 dated May 2, 2011.

All values are Renilla RLU/Firefly RLU

Distribution of Individual Mouse Values (ratios)

(Chen Caifu/ABI Method: Nucleic Acid Research, 2005, 33(20):e179)

A

B

C

All values are Renilla RLU/Firefly RLU

Distribution of Individual Mouse Values (ratios)

Figure 10. Distribution of Individual Mouse HBsAg Levels (normalized)
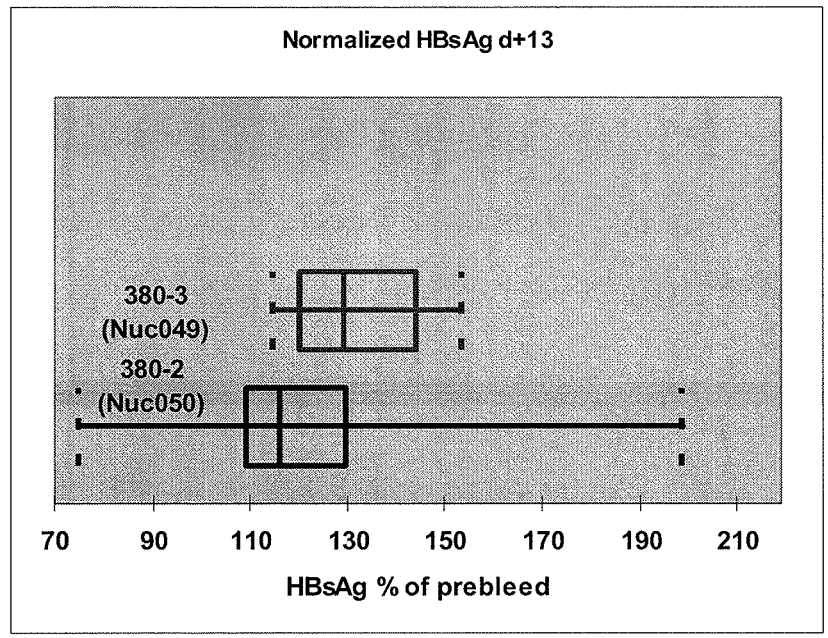
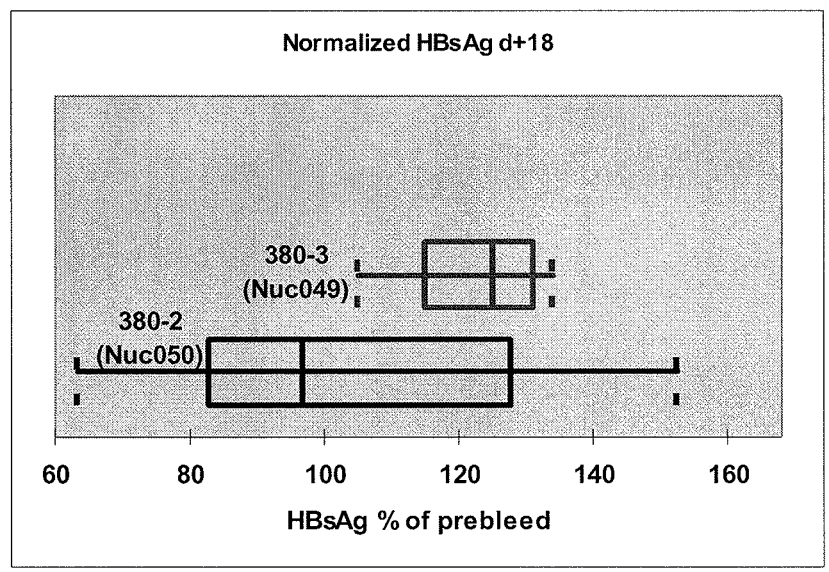

IN VIVO DELIVERY OF DOUBLE STRANDED RNA TO A TARGET CELL

CROSS-REFERENCE TO RELATED APPLICATIONS

This application is the U.S. national phase application of International Application No. PCT/US2007/083805, filed Nov. 6, 2007, and claims benefit of priority to provisional application 60/857,501 filed Nov. 8, 2006, provisional application 60/907,014 filed Mar. 16, 2007, provisional application 60/956,610 filed Aug. 17, 2007, and provisional application 60/974,695 filed Sep. 24, 2007, and provisional application 60/978,950 filed Oct. 10, 2007. The international and provisional applications are herein incorporated by reference in their entireties.

FIELD OF INVENTION

The invention relates to methods of RNA-mediated inhibition of target polynucleotides in mammalian cells. This includes endogenously expressed siRNA, shRNA, miRNA, antisense nucleic acids, and ribozymes as well as exogenously delivered synthetic siRNA, shRNA, miRNA, antisense nucleic acids and ribozyme molecules. The methods also apply to providing functional RNA including mRNA for gene therapy indications. More particularly, it relates to methods of inhibiting the function of a target polynucleotide in a target mammalian cell in vivo comprising introducing into a first cell such as a skin cell, muscle tissue cell, including skeletal or striated muscle cells (myocyte or myoblast), or any other competent cell of the mammal double stranded RNA (dsRNA) or polynucleotide expression construct encoding one or more dsRNA or RNAi agent(s) including siRNA, shRNA, miRNA or other dsRNA, such that the RNAi agent is delivered distally to the target cell.

BACKGROUND OF THE INVENTION

The ability of double stranded RNA to effectively silence gene expression, a phenomenon now commonly known as RNA interference (RNAi), has been one of the biggest scientific findings of the past decade. Recently, scientists Andrew Fire and Craig Mello were awarded the 2006 Nobel Prize for Medicine for their pioneering work in the RNAi field. However, many challenges still remain to move RNAi from the laboratory to the clinic. The biggest challenge to RNAi-mediated inhibition of target gene expression in animals and particularly humans is the efficient delivery of the RNAi agent to a sufficient number of target cells. A variety of delivery mechanisms are currently being explored in the RNAi field.

For instance, a number of groups have demonstrated successful and efficient delivery of double stranded (ds) RNA to mouse liver by tail vein injection. McCaffrey et al. (Nature Biotechnol. (2003) 21(6): 639-44) report inhibiting production of hepatitis B virus replicative intermediates in mice following tail vein injection of plasmids expressing HBV specific short hairpin RNAs (shRNAs). Giladi et al. (Mol. Therapy (2003) 8(5): 769-76) also report inhibition of HBV replication in mice following tail vein injection of HBV specific short interfering RNA (siRNA), and Song et al. (Nature Med. (2003) 9(3): 347-51) report RNA interference of fulminant hepatitis in mice following tail vein injection of siRNA specific for the fas gene.

While tail vein injection is suitable for inhibiting gene expression in mice, it is not a clinically relevant technique that may be used for humans. However, several groups have also shown successful delivery of dsRNA therapeutics without tail vein injection by systemic delivery using synthetic dsRNAs with improved stability. See Soutschek et al. Nature (2004) 432(7014): 173-8; see also Morrissey et al. Hepatol. (2005) 41(6): 1349-56. Local administration to the liver has also been demonstrated by injecting double stranded RNA directly into the circulatory system surrounding the liver using renal vein catheterization. See Hamar et al. PNAS (2004) 101(41): 14883-8. Still others have reported successful delivery of dsRNA and particularly siRNA using cationic complexes or liposomal formulations. See, e.g., Landen et al. Cancer Biol. Ther. (2006) 5(12); see also Khoury et al. Arthritis Rheumatol. (2006) 54(6): 1867-77.

In addition to injection into the circulatory system and lipid-based means of delivering dsRNA, several groups have reported the use of retroviral and adenoviral vectors for introducing dsRNA into mammals. For instance, Van den Haute et al. (Human Gene Therapy (2003) 14: 1799-1807) report lentiviral vector delivery of short hairpin (shRNAs) against the reporter enhanced GFP (EGFP) that were shown to knock down gene expression of EGFP in mouse brain up to six months after transduction. McCaffrey et al. (Abstract No. 039, Keystone Symposia on siRNAs and miRNAs, Apr. 14-19, 2004) report intravenous infusion of recombinant adenoviruses expressing HBV-specific shRNAs in HBV infected mice as a possible treatment approach against hepatitis virus infection in animals.

Thus, although some success has been shown using localized delivery, or by using systemic delivery of stabilized or complexed dsRNA, there is still a great need for in vivo RNAi delivery mechanisms that do not require specialized formulations or invasive delivery procedures. Furthermore, the present inventors have shown that DNA-based endogenous delivery of dsRNA is especially advantageous in allowing one to avoid the interferon/PKR response while providing a prolonged supply of expressed dsRNA. See US 2004/0152117, which is herein incorporated by reference in its entirety. Accordingly, there is a particular need for targeted delivery mechanisms for DNA-based RNAi expression vectors that do not require the use of viruses.

RNA interference was first discovered in the nematode C. elegans by Nobel prize laureates Andrew Fire and Craig Mello and their colleagues. See U.S. Pat. No. 6,506,559, which is herein incorporated by reference. In US '559, Fire and Mello et al. report that dsRNA-mediated inhibition showed a surprising ability to cross cellular boundaries. This observation has since been described as a phenomenon that is particular to nematodes or invertebrates, and corresponding modes of such RNAi trafficking in vertebrate organisms have been generally dismissed.

The present inventors have surprisingly discovered, however, that intramuscular, intradermal and subcutaneous delivery of expression constructs encoding dsRNA results in targeted inhibition of gene expression in vivo in the liver and potentially other organs and tissues of mammalian organisms. Without wishing to be bound by any theory, the inventors hypothesize that delivery of dsRNA to the liver from the muscle or skin, for example, may be mediated by extracellular vesicles (exovesicles) containing expressed RNA molecules such as dsRNA, antisense, miRNA, or mRNA or injected/introduced RNA molecules such siRNA, shRNA, etc. that bud from the surface of transfected muscle cells. The extrusion of such exovesicles has been demonstrated for several cell types including muscle.

There is evidence in the art that certain lectins are exported from muscle cells and myoblasts through evaginations of the cell membrane which pinch off to form extracellular vesicles called exovesicles. Such lectins including beta galectins are known to be on the surface of the extruded exovesicles. See Cooper and Barondes, Evidence of export of a muscle lectin from cytosol to extracellular matrix and for a novel secretory mechanism. J. Cell Sci. (1990) 110: 1681-91; see also Harrison and Wilson, The 14 kDa beta-galactoside binding lectin in myoblast and myotube cultures: localization by confocal microscopy, J. Cell Sci. (1992) 101(Pt. 3): 635-46. Extracellular vesicles have also been observed at the periphery of fibroblasts, which are present in high quantity in the dermal layer of the skin. See Mehul and Hughes, 1997, Plasma membrane targeting, vesicular budding, and release of galectin 3 from the cytoplasm of mammalian cells during secretion, J. Cell Sci. 110: 1169-78. There is also evidence that lectins and certain glycoproteins may be cleared from the circulation by specific receptors on the surface of liver cells. See, e.g., Park et al., The asialoglycoprotein receptor clears glycoconjugates terminating with sialic acid alpha 2,6GalNAc. PNAS (2005) 102(47): 17125-9; see also Nagaoka et al., Galectin receptors are known to be expressed on the surface of hepatocytes. Furthermore, betagalectin receptors have been shown to be expressed in a polarized manner on the sinusoidal side of the hepatocytes, "A quantitative analysis of lectin binding to adult rat hepatocytes cell surfaces", In Vitro Cellular and Developmental Biology (1988) 24: 401-412; "Participation of a galectin-dependent mechanism in the hepatic clearance of tissue-type plasminogen activator and plasma kallikrein." Thromb Res (2003) 108: 257-262.

Thus, the present inventors propose that cytosolic content including RNAs, e.g., mRNA, expressed siRNA/shRNA/miRNA, as well as injected/introduced siRNA/shRNA/miRNA, or possibly even transfected DNA present in the cytosol can be packaged within these exovesicles and be transported to distal sites such as the liver. Other mechanisms of transfer have not been ruled out. Whatever the mechanism, to the present inventors' knowledge, no one has recognized or proposed that intramuscular, intradermal or subcutaneous administration of dsRNA and particularly expressed dsRNA may be used in vivo in mammalian organisms as a therapeutic nucleic acid delivery mechanism for liver diseases as well as diseases affecting other distal organs and tissues.

SUMMARY OF INVENTION

The present invention encompasses methods of delivering nucleic acids, including double stranded RNA molecules and/or polynucleotide expression constructs encoding RNA molecules, e.g., mRNAs, antisense, ribozyme or dsRNA including RNAi agents such as siRNA, shRNA, or miRNA, to a target cell in vitro or ex vivo by delivering a nucleic acid to or expressing a nucleic acid in a cell that is competent for distal cell targeting. The cell may then be utilized for production in cell culture of RNA-containing exovesicles, or for autologous or heterologous transplant into a recipient mammalian organism. The cell may be a stem cell.

In one embodiment, among others, the invention includes methods of delivering at least one double stranded RNA (dsRNA) to a target cell in an animal comprising transfecting a first cell in the animal other than said target cell with a nucleic acid encoding said dsRNA, wherein said transfection results in the dsRNA being delivered to the target cell. The nucleic acid encoding the dsRNA may be cotransfected with a nucleic acid expressing a transmembrane or surface ligand specific for said target cell, either on a single vector or via separate nucleic acid constructs.

The methods of the present invention may be used to deliver any nucleic acid that is capable of being delivered from the transfected cell to a distal target cell. In some embodiments, the nucleic acid is a polynucleotide expression construct, e.g., a DNA plasmid or viral vector, which encodes an RNA effector molecule, e.g., an RNAi molecule comprising a dsRNA region homologous and complementary to a target gene in said distal organ or tissue (for instance, for mediating RNA interference or RNAi), or another biologically active RNA. Suitable expressed dsRNA or RNAi molecules include shRNA, siRNA and miRNA and are typically between about 34 to about 500 bases in length and include double stranded or partially double stranded regions of at least about 15 basepairs, typically 19 to 29 basepairs; mRNAs sizes typically range from about 700 nts to about 15,000 nts in length.

In one embodiment, among others, the present invention encompasses methods of delivering nucleic acids to distal organs and tissues via intramuscular administration and transfection of muscle cells with at least one type of nucleic acid in vivo. For instance, the invention includes a method of delivering at least one double stranded RNA (dsRNA) to a target organ or tissue in an animal comprising transfecting skeletal muscle cells in said animal with a nucleic acid encoding said dsRNA, wherein said transfection results in said dsRNA being delivered to said target tissue or organ. When skeletal muscle cells are transfected, the target organ or tissue is an organ or tissue or cell other than skeletal muscle. In some embodiments, a skeletal muscle cell is transfected with an expression construct encoding a dsRNA molecule, the dsRNA molecule is expressed in the skeletal muscle cell, and the dsRNA molecule is delivered to a target cell that is not a skeletal muscle cell.

In another embodiment, among others, the present invention encompasses methods of delivering nucleic acids to distal organs and tissues via intradermal or subcutaneous administration and transfection of skin cells including fibroblasts with at least one type of nucleic acid in vivo. For instance, the invention includes a method of delivering at least one double stranded RNA (dsRNA) to a target organ or tissue in an animal comprising transfecting skin cells in said animal with a nucleic acid encoding said dsRNA, wherein said transfection results in said dsRNA being delivered to said target tissue or organ. When skin cells are transfected, the target organ or tissue is an organ or tissue or cell other than the skin. In some embodiments, a skin cell is transfected with an expression construct encoding a dsRNA molecule, the dsRNA molecule is expressed in the skin cell, and the dsRNA molecule is delivered to a target cell that is not a skin cell.

While some embodiments encompass transfecting skeletal muscle cells, skin cells or other competent cells in an animal with a nucleic acid encoding a dsRNA, methods wherein dsRNA is directly transfected into muscle cells, skin cells or other competent cells are also encompassed. These dsRNA molecules include exogenously prepared transcribed and synthetic siRNA, shRNA and or miRNA molecules, including chemically modified RNAs. For instance, the invention includes a method of delivering at least one dsRNA to a target organ or tissue in an animal comprising transfecting skeletal muscle cells, skin cells or other competent targeting cells in said animal with said dsRNA, wherein said transfection results in said dsRNA being delivered to said other target organ or tissue. Suitable dsRNA molecules include shRNAs, siRNAs, and miRNAs and are typically between about 34 to about 500 nucleotides, preferably comprising at least 15 to 29 basepairs in double-stranded conformation, including in some applications as miRNAs certain mismatches. The methods of the invention may be performed so as not to trigger an interferon/PKR response, for instance by using shorter dsRNA molecules between 19 to 29 base pairs, or by using other methods known in the art. See US Publication 2004/0152117, which is herein incorporated by reference. The RNAs may be chemically modified as known in the art to increase stability and decrease non-specific effects and toxicity.

Applicants have also demonstrated that dsRNA molecules, including long dsRNA molecules (e.g., at least about 60, about 75, about 100, about 150, about 200, about 300, about 400, about 500, about 600 bp and greater), may be expressed intracellularly in stress-response competent mammalian cells (e.g., non-embryonic, differentiated or adult cells) without any evidence of their inducing an interferon, stress, or "panic" response, see US 2004/0152117A1, which is herein incorporated by reference in its entirety. In addition, the methods of the invention may themselves serve to minimize or avoid triggering a stress response in the target cell to which the dsRNA is delivered irrespective of the length or nature of the dsRNA; e.g, dsRNAs delivered into distal cells within "blebs" may avoid triggering a stress response, in contrast to the same dsRNAs entering through the cell membrane without the cover of the surrounding "bleb". Any molecule that may be conjugated to dsRNA, co-transfected or co-expressed therewith, and delivered therewith to the target cell may be included.

The present invention also encompasses methods of treating or preventing diseases in distal organs or tissues in an animal via intramuscular, intradermal or subcutaneous administration or transfection of other competent targeting cells, with at least one nucleic acid in vivo. For instance, the invention includes a method of treating or preventing disease in a target organ or tissue in an animal, comprising transfecting skeletal muscle cells, skin cells or other competent non-target cells in said animal with a nucleic acid encoding a dsRNA corresponding to a target gene in a cell of said target organ or tissue, wherein said transfection results in said dsRNA being delivered to said target tissue or organ, and wherein delivery of said dsRNA to said target organ or tissue inhibits or reduces expression of said target gene in said target organ or tissue thereby treating or ameliorating said disease. "Intramuscular", "intradermal", or "subcutaneous" delivery as defined herein includes any method which achieves transfection of cells within the identified tissue, including without limitation needle injection into the tissue itself or delivery into a blood vessel which supplies the tissue, intravascular delivery into a vessel having enhanced permeability, needleless injection, biolistic or gene gun projection into a cell or tissue, any of the various known injection/electroporation technologies, transdermal patch, etc.

Administration may be via any method or device which can achieve the desired introduction of polynucleotide, e.g., needle, syringe, catheter or cannula injection or needleless injection, e.g., a Bioject needleless injection device, which can be adjusted to deliver a liquid medication to various depths including intradermal, subcutaneous, and/or intramuscular. A transdermal patch might also be employed, as well as a biolistic injector or "gene gun" device capable of shooting a plasmid expression vector into cells. Any of the various injection/electroporation devices and technologies (Inovio/Genetronics, Ichor, VGX etc.) may also be used, as may hydrodynamic intravascular methods which utilize various means, e.g., increased permeability/increased pressure, to promote delivery to cells including muscle, e.g., the Mirus Pathway IV™ Gene Delivery methods (Minis, Madison, Wis.) which utilize a cuff or tourniquet to restrict blood flow and increase pressure within the vessel in order to facilitate intravascular delivery of nucleic acids such as plasmid expression vectors to tissues perfused by the vessel, e.g., limb muscle. A syringe, pump or other suitable device may be used to effect rapid intravascular delivery while blood flow is transiently occluded, thereby promoting transfection of the adjoining muscle cells.

The methods of the present invention are particularly suitable for treating or preventing diseases or conditions of or involving the liver including viral diseases of the liver, liver cancer and genetic diseases of the liver, or conditions which may be modulated by targeting an RNA or gene in the liver via e.g. antisense or RNA interference, or gene therapy where a functional mRNA is replaced. Expressed therapeutic mRNAs and proteins may also be delivered to target cells via the methods of the present invention. The methods are also appropriate for targeting genes in the liver responsible for certain metabolic diseases or disorders such as high cholesterol levels for example, including but not limited to apolipoprotein B and pcsk9. The methods may also be used to deliver nucleic acid-based therapeutics to other cells and organs or tissues, including cancer cells or HIV-infected cells, for instance by expressing suitable receptors or other ligands on the surface of target cells, and/or by co-expressing cell surface or exovesicular-targeted ligands in transfected competent targeting cells. The methods may also be used prophylactically, for instance to deliver dsRNAs or other nucleic acid-based therapeutics to target cells to protect against future infection or disease.

BRIEF DESCRIPTION OF THE DRAWINGS

FIG. 10. Distribution of individual mouse normalized HBsAg levels for NUC 049 versus NUC050 at day 6 (13 days after vector injection) and day 11 (18 days after vector injection).

DETAILED DESCRIPTION OF INVENTION

Figure 1:
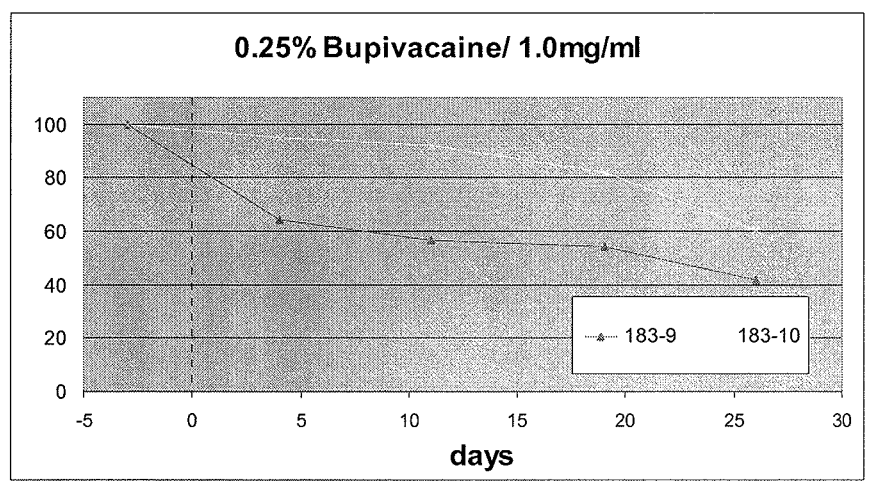
FIG. 1. Graph demonstrating the percent decrease in HBsAg expression mediated by the NUC050 vector, which expresses four HBV-targeted short hairpin dsRNAs, (experiment 183-9) compared to control vector (183-10) in $NOD^{scid}$ mice. Mice were administered either NUC050 plasmid (183-9) or negative control plasmid NUC049 (183-10), formulated with bupivacaine and injected intramuscularly (IM) at day 0. Both groups of mice received a hydrodynamic injection (HDI) of HBsAg expression plasmid NUC054 at day −5. Serum sAg levels were measured at various days after dosing. Values represent mean sAg as a percent of the pre-bleed sAg value for each group of animals.

The present invention encompasses methods of delivering RNA including double stranded RNA (dsRNA) to a distal target cell or organ or tissue by expressing the RNA (e.g., a dsRNA) in, or introducing the RNA into, a first cell that is competent for inter-organ or inter-tissue or intercellular delivery. By "distal" is meant that the RNA, e.g., a dsRNA is transported to a different organ, tissue or cell than the cell into which it is originally introduced or expressed. "Competent for inter-organ or inter-tissue or intercellular delivery" or "competent for targeting a distal cell or organ or tissue" means that the cell into which the dsRNA is expressed or introduced is able to facilitate delivery of the dsRNA to a distal organ, tissue or cell, e.g., through vesicle extrusion. Such cells include muscle cells and skin cells, and any other cell that is competent for RNA delivery to distal tissues.

The present invention is based on the surprising discovery that intramuscular, intradermal or subcutaneous injection of a nucleic acid encoding a dsRNA corresponding to a target gene results in inhibition of target gene expression in the liver. Accordingly, in one embodiment, the invention encompasses methods of delivering nucleic acids to distal organs or tissues in vivo and methods of treating or preventing diseases and disorders in distal organs or tissues via intramuscular, intradermal or subcutaneous administration and transfection of muscle or skin cells with at least one dsRNA, or at least one nucleic acid expressing a dsRNA corresponding to a target gene in a cell of said distal organ or tissue.

As reported herein, the present inventors have demonstrated that intramuscular, intradermal or subcutaneous delivery of a vector or DNA construct expressing target-specific dsRNA molecules, e.g., shRNA (RNAi) molecules, is surprisingly able to reduce the expression of Hepatitis B surface antigen (sAg), as well as other target genes, in the liver. While not wishing to be bound by any mechanism, it is hypothesized that the encoded double-stranded RNA molecules (e.g., shRNAs or duplex dsRNAs) are transcribed from expression constructs transfected into muscle or skin cells and the RNAi molecules are then delivered to the liver. While no evidence has been found that any significant quantity of intact dsRNA expression plasmid DNA itself gets into liver hepatocytes, it cannot yet be ruled out that DNA encoding the double-stranded molecules of the invention is transferred to the liver, either alone or in combination with the expressed dsRNA.

Muscle cells are one type of cell known to extrude plasma membrane vesicles, or exovesicles, also known as membrane "blebbing". For example, galectin is one protein expressed at high levels in skeletal and smooth muscle cells, which lacks a signal sequence and has been shown to be secreted by a mechanism distinct from classical exocytosis. Prior to secretion, galectin has been observed to become specifically concentrated under the myoblast plasma membrane and in plasma membrane evaginations which appear to pinch off to form galectin rich extracellular vesicles. Cooper and Barondes, 1990; Cooper, 1997, Galectin-1: Secretion and Modulation of Cell Interactions with Laminin, Trends in Glycoscience and Glycotechnol. 9(45): 57-67; Harrison and Wilson, 1992, The 14 kDa β-galactosidase binding lectin in myoblast and myotube cultures: localization by confocal microscopy, J. Cell Sci. 101: 635-46.

Although the process of membrane blebbing and the extent to which membrane blebbing contributes to protein export in other cell types are still unclear, membrane blebbing has also been observed in cells other than muscle cells. Indeed, a variety of different galectin genes have been detected in different cell types, each lacking a signal sequence and containing a highly conserved core sequence of about 130 amino acids. See Cooper and Barondes, 1999. Galectin-1, the best-characterized of the galectin family, is expressed in many tissues besides skeletal and smooth muscle, including liver, lung, heart, spleen, intestine, brain, lymphocytes, thymocytes and other vascular cells, the olfactory system, and the central and peripheral nervous systems. Inagaki et al. 2000, Oxidized galectin-1 promotes axonal regeneration in peripheral nerves but does not possess lectin properties, European J. Biochem. 267(10): 2955-64. Galectin-1 is also expressed and secreted by CHO cells by a non-classical mechanism. See Seelenmeyer et al., 2005, Cell surface counter receptors are essential components of the unconventional export machinery of galectin-1, J. Cell Biol. 171: 373-81. Galectin-3, which has also been shown to be secreted in exovesicles that pinch off the plasma membrane, has been detected in activated macrophages, eosinophils, neutrophils, mast cells, the epithelium of the gastrointestinal and respiratory tracts, the kidneys and some sensory neurons as well as many tumors. Krzeslak and Lipinska, 2004, Galectin-3 as a multifunctional protein, Cell. Mol. Biol. Letts. 9: 305-28.

Membrane blebbing, sometimes referred to as ectocytosis, has been observed at the periphery of many cell types, including fibroblasts, neutrophils and chondrocytes. See Mehul and Hughes, 1997, Plasma membrane targeting, vesicular budding, and release of galectin 3 from the cytoplasm of mammalian cells during secretion, J. Cell Sci. 110: 1169-78. Further, it has been hypothesized that shedding of membrane exovesicles may also be a mechanism for FGF-2 secretion from a variety of other cell types. See Walter Nickel 2005 Unconventional Secretory Routes: Direct Protein Export Across the Plasma Membrane of Mammalian Cells, Traffic 6: 607-14. Also, membrane blebbing has also been proposed as a potential secretory mechanism for certain apocrine-synthesized proteins, including secretory transglutaminase. See Aumuller et al. 1999 Apocrine secretion—Fact or artifact? Ann. Anat. 181(5): 437-46. Assuming membrane blebbing is involved in the effects reported in the present invention, the methods of the present invention may be performed using any exovesicle-producing cell that is currently known or that will be identified in the future. Since extruded exovesicles are on average about 80 nm in diameter and coated with surface galectins, they have the potential to interact with cell types that contain galectin receptors. Such cells include hepatocytes, whose galectin receptors are positioned to face the sinusoids and thus be exposed to molecules and particles in the blood.

Exovesicles, which generate as a process of membrane blebbing or shedding, should be distinguished from exosomes or multivesicular bodies. See Walter Nickel 2005; see also Cooper, 1997. Exosomes are produced from the endoplasmic reticulum and have very little if any cytosolic content, although they do have some MHC molecules on their surface and can be used as antigen presenting vehicles. In contrast, exovesicles bud from the surface of muscle cells and include cytosolic content as has been demonstrated by the inventors. Indeed, in the process of expressed interfering RNA (eiRNA), transcription occurs in the nucleus but the RNA is then transported to the cytoplasmic compartment, where the inventors hypothesize it is then incorporated into exovesicles blebbing off the membrane surface.

Notwithstanding the actual mechanism, the present invention encompasses methods of delivering at least one nucleic acid to a target cell in an animal comprising transfecting a first cell in the animal other than said target cell that is competent for distal cell targeting with a nucleic acid encoding an RNA of interest, e.g., an "RNA effector molecule" having a desired biological activity, e.g., an antisense RNA, triplex-forming RNA, ribozyme, an artificially selected high affinity RNA ligand (aptamer), a double-stranded RNA (e.g., siRNA, shRNA, miRNA) or other regulatory RNA or an mRNA, wherein said transfection results in either the DNA or the encoded RNA being delivered to the target cell. The RNA may or may not be polyadenylated. The RNA may or may not be capable of being translated. The first competent cell may also be transfected in vitro or ex vivo, and the competent cell thereafter introduced into the animal. The methods of the present invention may be used to deliver any nucleic acid that is present in the cytoplasm of the transfected cell and is capable of being delivered to the distal target cell. In addition to transfected and expressed dsRNAs, the present invention also includes methods of delivering expressed mRNA from therapeutic genes. RNAs that may be delivered to the distal target cell include, but are not limited to, antisense RNA, ribozyme RNA, dsRNAs including hairpin dsRNA, microRNA and duplex dsRNA molecules, as well as mRNAs.

Suitable "competent" cells for use in the methods of the invention include muscle cells, skin cells and any other competent cell capable of delivering nucleic acids to a distal target cell. Other competent cells may be identified using one of the RNA transfer assays disclosed in WO 00/63364, which is herein incorporated by reference in its entirety. For instance, Example 2 of WO 00/63364 describes two different in vitro assays that may be used to detect the transfer of RNA molecules between co-cultured donor and target cells.

By "double stranded RNA" or "dsRNA" is meant a ribonucleic acid containing at least a region of nucleotides that are in a double stranded conformation. The dsRNA may be a conventional siRNA, shRNA or miRNA (including primary transcript or pri-miRNA, pre-miRNA, or functional miRNA) or an RNA that contains more than one hairpin structure. The double stranded RNA may be a single molecule with one or more region(s) of self-complementarity such that nucleotides in one segment of the molecule base pair with nucleotides in another segment of the molecule. In various embodiments, a double stranded RNA that consists of a single molecule consists entirely of ribonucleotides, a combination of ribonucleotides and modified bases, or includes a region of ribonucleotides that is complementary to a region of deoxyribonucleotides. Alternatively, the double stranded RNA may include two different strands that have one or more region(s) of complementarity to each other. Desirably, the region of the double stranded RNA that is present in a double stranded conformation includes at least about 15 to 20, 20 to 25, 25 to 30, 50, 75, 100, 200, 500, 1000, 2000 or 5000 nucleotides participating in one strand of the double stranded structure, or includes all of the nucleotides being represented in the double stranded RNA. In some embodiments, the double stranded RNA is fully complementary, and does not contain any single stranded regions, such as single stranded ends. In other embodiments, as e.g., miRNA-type dsRNA molecules, the double-stranded regions may be interspersed with one or more single-stranded nucleotides or areas. In some embodiments the dsRNA is an shRNA. All such synthetically prepared and exogenously delivered RNAs, including shRNAs and duplex or siRNAs, may be chemically stabilized and chemically modified, using one or more of the methods and chemical modifications known to those of skill in the art. Such modifications which may be used in combination include sulfur chemistry modification such as phosphorothioate linkages that make the drug more resistant to degradation, 2'-O-methoxyethyl modifications, etc. See e.g. Chiu and Rana, siRNA function in RNAi: A chemical modification analysis, RNA (2003), 9:1034-1048. Cold Spring Harbor Laboratory Press, the teaching of which is incorporated by reference.

In some embodiments, the dsRNA region of the RNA molecule corresponds to a target gene in said target organ or tissue (for instance, for mediating RNA interference or RNAi). In such instances, the dsRNA region is preferably not translated, and is substantially homologous and complementary to a region of the target gene. Where the dsRNA is used for RNA interference, one strand of the dsRNA structure or region, i.e., the antisense strand, will have at least about 70, 80, 90, 95, 98, or 100% complementarity to a target nucleic acid, and the other strand or region, i.e., the sense strand or region will have at least about 70, 80, 90, 95, 98, or 100% identity to a target nucleic acid. In such embodiments, the dsRNA is considered to be both substantially homologous and complementary to the target gene, meaning that the dsRNA need not be entirely identical and complementary to the target gene so long as it is still effective to mediate sequence specific RNA interference. Such dsRNAs will usually have a sequence of at least 19 contiguous nucleotides 100% complementary and homologous to a target nucleic acid. Preferred for RNAi applications are short hairpin dsRNA (shRNA) molecules and microRNA (miRNA) molecules. By shRNA (short-hairpin RNA) is meant an RNA molecule of less than approximately 400 to 500 nucleotides (nt), preferably less than 100 to 200 nt, in which at least one stretch of at least 15 to 100 nucleotides (preferably 17 to 50 nt, more preferably 19 to 29 nt) is base paired with a complementary sequence located on the same RNA molecule, and where said sequence and complementary sequence are separated by an unpaired region of at least about 4 to 7 nucleotides (preferably about 9 to about 15 nucleotides) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, preferably about 9 to about 15 nucleotides, which forms a single-stranded loop above the stem structure created by the two regions of base complementarity. In addition to single shRNAs, included shRNAs can be dual or bi-finger and multifinger hairpin dsRNAs, in which the RNA molecule comprises two or more of such stem-loop structures separated by a single-stranded spacer region. A recombinant vector may be engineered to encode multiple, e.g., three, four, five or more short hairpin dsRNAs and/or other RNAs such as mRNAs. The hairpin dsRNA may be a single hairpin dsRNA or a bi-fingered, or multi-fingered dsRNA hairpin as described in PCT/US03/033466 or WO 04/035766 or a partial or forced hairpin structure as described in WO 2004/011624, or the dsRNA may be a polynucleotide comprising one or more dsRNA effector molecules encoded in a miRNA context as described in PCT/US2007/81103 filed 11 Oct. 2007. The teachings of each of these documents are incorporated herein by reference in their entireties.

An siRNA can be expressed or synthetic and is comprised of two RNA strands that basepair with each other to form a dsRNA, i.e., duplex RNA. The basepairing does not need to be 100% and thus the complementarity of one strand with the second does not need to be 100%. Complementarity should be sufficient to maintain the stands in double-stranded confirmation. The amount of complementarity needed is sequence and length dependent and can be easily calculated by one skilled in the art. siRNA length is most optimally 19-29 bp, next preferred is 30-40 bp. A limited number of mismatches within the double-stranded region, especially in the sense strand, is compatible with RNAi activity. siRNAs may be chemically stabilized and chemically modified, using one or more of the methods and chemical modifications known to those of skill in the art.

By "target nucleic acid" is meant the nucleic acid sequence in the distal target organ, tissue or cell whose expression is modulated as a result of sequence-specific nucleic acid based inhibition, e.g., post-transcriptional or transcriptional gene silencing, antisense inhibition, ribozymal cleavage, etc. The target nucleic acid sequence can be any nucleic acid in the target cell, DNA, RNA or DNA/RNA hybrid, whose expression is desired to be modulated, including without limitation gene sequences or chromosomal sequences endogenous to the cell as well as introduced sequences, genomic sequences, cDNA, mRNA sequences, sequences of intracellular pathogens such as viral nucleic acids present in the cell, transcribed and non-transcribed sequences, coding and non-coding sequences, translated and non-translated sequences including 3' and/or 5' UTRs, and regulatory sequences such as transcription factor binding site, promoter, enhancer, and repressor sequences. Suitable target nucleic acid sequences are associated with cancer or abnormal cell growth, such as oncogenes, and nucleic acid sequences associated with an autosomal dominant or recessive disorders, as well as nucleic acid sequences associated with pathogens including viruses. To "modulate" means to decrease the expression of a target nucleic acid in a cell, or the biological activity of the encoded target polypeptide in a cell, by at least about 20%, more desirably by at least about 30%, 40%, 50%, 60%, 75%, 80%, 85%, 90%, 95% or even 100%. In some instances, expression of genes in the target cell may also be increased, for instance where the gene targeted by the dsRNA is a transcriptional repressor or other negative regulatory gene. In some instances the target nucleic acid will not be present in the first transfected cell. In some instances the target nucleic acid will be present in the first transfected cell as well as in the distal target cell.

Typically with expressed interfering RNA (eiRNA), the dsRNA is expressed in the first transfected cell from an expression vector. In such a vector, the sense strand and the antisense strand of the dsRNA may be transcribed from the same nucleic acid sequence using e.g., two convergent promoters at either end of the nucleic acid sequence or separate promoters transcribing either a sense or antisense sequence. Alternatively, two plasmids can be cotransfected, with one of the plasmids designed to transcribe one strand of the dsRNA while the other is designed to transcribe the other strand. Alternatively, the nucleic acid sequence encoding the dsRNA comprises an inverted repeat, such that upon transcription from a single promoter, the expressed RNA forms a double stranded RNA, i.e. that has a hairpin or "stem-loop" structure, e.g., an shRNA. The loop between the inverted repeat regions, or sense and antisense regions, is typically at least four base pairs, but can be at least about 10, at least about 15, at least about 20, at least about 25, at least about 30, at least about 50, or at least about 75, or more, or any size that permits formation of the double stranded structure. Multiple stem-loop structures may be formed from a single RNA transcript to generate a multi-target dsRNA. See WO 00/63364, and WO2004/035765, which are herein incorporated by reference in their entireties. Hairpin structures may be partial or forced hairpin structures as described in WO2004/011624, incorporated herein by reference.

By "expression vector" is meant a recombinant vector including a DNA or RNA construct or viral vector that contains at least one promoter operably linked to a sequence encoding a regulatory RNA such as a siRNA, shRNA, miRNA, antisense, or a downstream gene or coding region or other nucleic acid sequence to be transcribed (e.g., a cDNA or genomic DNA fragment that encodes a protein, optionally, operably linked to sequence lying outside a coding region, or a sense and/or an antisense RNA coding region, and/or RNA sequences lying outside a coding region). The sequence(s) to be transcribed may include any target nucleic acid sequence whose expression is desired to be modulated. Transfection or transformation of the expression vector into a recipient cell allows the cell to express RNA encoded by the expression vector. An expression vector may be a genetically engineered plasmid, viral vector including but not limited to AAV, adenovirus, poxvirus, herpesvirus, retrovirus, lentivirus, and alphavirus, or artificial chromosome derived from, for example, a bacteriophage, adenovirus, adeno-associated virus, retrovirus, poxvirus, or herpesvirus. Preferred for expression of dsRNA effector molecules in the methods of the invention are RNA polymerase III Type 3 or "U6-type" RNA polymerase III promoters and multiple RNA polymerase III promoter expression constructs as taught in WO 06/033756. RNA polymerase II promoters including mammalian viral promoters, and mammalian including human cellular promoters may be utilized for expression of longer RNAs including mRNAs. An expression construct can be replicated in a living cell such as a bacterium or eukaryotic cell or it can be made synthetically. For purposes of this application, the terms "expression vector", "expression construct", "vector", and "plasmid" are used interchangeably in the general illustrative sense and are not intended to limit the invention to a particular type of expression construct.

By "operably linked" is meant that a gene and one or more transcriptional regulatory sequences, e.g., a promoter or enhancer, are connected in such a way as to permit gene expression when the appropriate molecules (e.g., transcriptional activator proteins) are bound to the regulatory sequences.

By "promoter" is meant a minimal sequence sufficient to direct transcription of a gene. Also included in this definition are those transcription control elements (e.g., enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. Included are RNA pol I, RNA pol II and RNA pol III promoters, including RNA polymerase III Type 3 promoters such as H1, 7SK, and U6. Polymerase III Type 3 promoters may advantageously be used to express short oligonucleotides such as the shRNAs, siRNAs, and other oligonucleotide RNA effector molecules of no more than 300 to 400 nucleotides in length (see U.S. Pat. No. 5,624,802, Noonberg et al.). A preferred RNA pol III 7SK promoter (7SK 4A) and expression constructs comprising multiple polymerase III promoters are taught in WO 06/033756. Also included are promoters that permit overexpression of mRNAs in the cytoplasm of the transfected cell, for instance to optimize incorporation of expressed mRNA molecules into membrane exovesicles.

Expression plasmids that transcribe RNA effector molecules including dsRNAs in either the cytoplasm or the nucleus may be utilized. Expression vectors may be designed to integrate into the chromosome of transfected cells, for instance by homologous recombination. Alternatively, expression vectors may replicate in transfected cells extrachromosomally. Nuclear transcription vectors for protein expression are preferably designed to express polyadenylated 5' capped RNA (for example, a vector containing an RNA polymerase II promoter and a poly A site) to facilitate export from the nucleus. Intracellular transcription may also utilize bacteriophage T7 and SP6 promoters, i.e., by transfecting a vector that coexpresses the appropriate RNA polymerase gene, which may be designed to transcribe in the cytoplasm or in the nucleus. Promoters for viral RNA polymerases, either DNA and RNA dependent, may also be used. Alternatively, dsRNA replicating polymerases can be used. Promoters for cellular polymerases such as RNA Polymerase I, II, or III or mitochondrial RNA polymerase may also be utilized. Tissue- or cell-specific promoters may be used to limit expression of the dsRNA to the first transfected cell. Polymerase III promoters are especially desirable for expression of small engineered RNAs. See WO 06/033756, Multiple Polymerase III Promoter Expression Constructs, incorporated herein by reference. Preferred are polymerase III type 3 promoters, including various mammalian U6, H1, and 7SK promoters, including the modified 7SK 4A promoter sequence taught therein. See also, e.g., US 2005/0130184 A1, Xu et al., directed to modified polymerase III promoters which utilize polymerase II enhancer elements, as well as US 2005/0130919 A1, Xu et al., directed to regulatable polymerase III and polymerase II promoters, the teaching of which is hereby incorporated by reference. In some embodiments it may be desirable to include one or more polymerase I, and/or one or more polymerase II, and/or one or more polymerase III promoters in a single expression construct, as e.g., where it is desirable to utilize pol III promoters to express one or more RNA effector molecules such as dsRNAs and one or more pol II promoters to express one or more targeting ligands.

A desirable approach for cytoplasmic expression is to use endogenous polymerases such as the mitochondrial RNA polymerase to make dsRNA in the cytoplasm. These vectors are formed by designing DNA expression constructs that contain mitochondrial promoters upstream of the sequence encoding the dsRNA. As described above for nuclear transcription vectors, dsRNA can be generated using two such promoters placed on either side of the target sequence, such that the direction of transcription from each promoter is opposing each other. Alternatively, two plasmids can be cotransfected. One of the plasmids is designed to transcribe one strand of the target sequence while the other is designed to transcribe the other strand. Single promoter constructs may be developed such that two units of the target sequence are transcribed in tandem, such that the second unit is in the reverse orientation with respect to the other. Alternate strategies include the use of filler sequences between the tandem target sequences.

Cytoplasmic expression of dsRNA may also be achieved by transcription of a single stranded RNA template in the nucleus of the transfected cell, which is then transported into the cytoplasm where it serves as a template for the transcription of dsRNA molecules, utilizing a single subgenomic promoter opposite in orientation with respect to the nuclear promoter. The nuclear promoter generates one RNA strand that is transported into the cytoplasm, and the singular subgenomic promoter at the 3' end of the transcript is sufficient to generate its antisense copy by an RNA dependent RNA polymerase to result in a cytoplasmic dsRNA species. Both cytoplasmic and nuclear transcription vectors may contain a reporter gene to enable monitoring of cells that have taken up the plasmid. Any type of vector may be used, including plasmids, viral vectors, retroviral vectors, adenoviral vectors, AAV vectors, etc. The use of expression vectors to express double stranded RNA is also discussed in detail in US 20040152117, which is herein incorporated by reference in its entirety.

If desired, inducible and repressible transcription systems can be used to control the timing of the synthesis of RNA effector molecules including mRNAs. Inducible and repressible regulatory systems involve the use of promoter elements that contain sequences that bind prokaryotic or eukaryotic transcription factors upstream of the sequence encoding dsRNA. In addition, these factors also carry protein domains that transactivate or transrepress the RNA polymerase II. The regulatory system also has the ability to bind a small molecule (e.g., a coinducer or a corepressor). The binding of the small molecule to the regulatory protein molecule (e.g., a transcription factor) results in either increased or decreased affinity for the sequence element. Both inducible and repressible systems can be developed using any of the inducer/transcription factor combinations by positioning the binding site appropriately with respect to the promoter sequence. Examples of previously described inducible/repressible systems include lac, ara, Steroid-RU486, and ecdysone-Rheogene, Lac (Cronin et al. Genes & Development 15: 1506-1517, 2001), ara (Khlebnikov et al., J. Bacteriol. 2000 December; 182(24):7029-34), ecdysone (Rheogene, www.rheogene.com), RU48 (steroid, Wang X J, Liefer K M, Tsai S, O'Malley B W, Roop D R., Proc Natl Acad Sci USA. 1999 Jul. 20; 96(15):8483-8), tet promoter (Rendal et al., Hum Gene Ther. 2002 January; 13(2):335-42. and Lamartina et al., Hum Gene Ther. 2002 January; 13(2):199-210), or a promoter disclosed in WO 00/63364, filed Apr. 19, 2000.

In one embodiment, among others, the present invention encompasses methods of delivering nucleic acids to distal organs or tissues via intramuscular, intradermal or subcutaneous administration and transfection of muscle or skin cells with at least one nucleic acid in vivo. When transfecting muscle cells, the expression construct comprises polynucleotide sequences encoding the double stranded RNA that are operably linked to regulatory elements operable in the muscle cell. When transfecting skin cells, the expression construct comprises polynucleotide sequences encoding the double stranded RNA that are operably linked to regulatory elements operable in the skin cell. Promoters and other regulatory elements operable in muscle and/or skin cells are known in the art, and for instance include, but are not limited to polymerase I, polymerase II, and polymerase III promoters (e.g., preferably pol III type 3 promoters including human and other mammalian U6, 7SK, and H1 promoters) as well as mitochondrial promoters, e.g., human and other mammalian mitochondrial heavy and light chain promoters. Short RNAs (fewer than 300-400 nt engineered RNAs such as shRNAs) are best expressed by pol I and/or pol III promoters. Longer RNAs, including mRNAs, are best expressed by pol II promoters, including viral promoters such as CMV IEP, RSV LTR, SV40, etc. Bacteriophage promoters such as T7, T3, SP6, etc. may also be utilized if the cell is also provided with the cognate T7, T3, SP6 polymerase(s). For expression in muscle and/or skin cells, such polymerase III promoters can be used to express small dsRNAs and polymerase II promoters such as CMV (cytomegalovirus immediate early promoter) including HCMV (human), MCMV (murine), SCMV (simian), SV40, RSV, vaccinia, and other viral promoters; eukaryotic including mammalian polymerase II promoters such as the B-actin promoter, can be used to express a translatable mRNA encoding a cell-surface protein, receptor, or targeting ligand or other desired protein. The mRNA may be translated in the first cell and/or a distal cell to which it is delivered.

Muscle cells include mammalian striated or skeletal myocytes, including differentiated myocytes as well as undifferentiated myoblasts. Cardiac muscle is also striated muscle. A myoblast is a type of stem cell that exists in muscles. Skeletal muscle cells are called muscle fibers or myocytes and are produced when myoblasts fuse together. Therefore, muscle fibers may have multiple nuclei. Myoblasts that do not form muscle fibers differentiate into satellite cells. These satellite cells remain adjacent to a muscle fiber, separated only by its cell membrane and by the endomycium (the connective tissue of collagen surrounding the muscle fiber).

"Intramuscular" administration means that the nucleic acid is administered to muscle tissue and any muscle cell in the animal, including but not limited to skeletal muscle such as the deltoid, vastus lateralis, ventrogluteal, tibialis and dorsogluteal muscles. The means by which intramuscular administration may be achieved includes needle injection, needleless injection, electroporation, biolistic approaches, and any other method that can accomplish delivery into a muscle cell or a cell in muscle tissue. Such delivery may be directly into the muscle tissue or via intravascular delivery into muscle cells or into cells in muscle tissue supplied by such blood vessel(s). In the methods of the invention comprising intramuscular administration, the RNAi agent or expressed dsRNA or other nucleic acid-based therapeutic is designed to inhibit the function of a target polynucleotide in a cell of the mammal which is not a muscle cell.

In one aspect of the invention, such an expression construct encoding sequences homologous and complementary to one or more target polynucleotide sequences present in a liver cell is introduced into a skeletal or other muscle cell and the function of one or more target polynucleotides in a liver hepatocyte is inhibited, e.g., polynucleotides of a liver pathogen such as a hepatitis virus, including HBV and/or HCV and HDV and HAV. In another aspect, the invention involves introducing into an appropriate cell such as a muscle cell an expression construct encoding sequences targeting genes in the liver responsible for metabolic diseases or disorders such as high cholesterol levels for example, including but not limited to apolipoprotein B and pcsk9. Another such potential liver target is the genetic disorder alpha 1-antitrypsin deficiency ($\alpha$1-antitryspin deficiency, A1AD or Alpha-1), caused by a mutation which results in defective production of alpha 1-antitrypsin (A1AT), leading to decreased A1AT activity in the blood and lungs, and deposition of excessive abnormal A1AT protein in liver cells. Treatment utilizing the methods of the invention would include providing an inhibitory dsRNA which targets the mutated A1AT sequence, while co-expressing an mRNA encoding the functional A1AT. This could be accomplished by providing to muscle cells an expression vector(s) co-expressing the inhibitory dsRNA and an mRNA encoding the functional protein, both of which are delivered to liver cells.

"Intradermal" administration means in or into the skin, and can include administration to any layer of the dermis or epidermis, and delivery into any cell thereof. "Subcutaneous" administration means just under the skin, or to the subcutaneous layer of the skin, and delivery into any cell thereof Also encompassed are epicutaneous forms of administration, i.e., with "epicutaneous" meaning on the surface of the skin (for instance using a transdermal patch, ointment, lotion or any other suitable means). Skin cells include cells of the epidermis, including for example basal cells, melanocytes, Langerhans' cells, Merkel cells, sensory nerves, keratinocytes, and any other cell found in the various layers of the epidermis including the basal layer, the squamous cell layer, the stratum granulosum, the stratum lucidum and the stratum corneum. Skin cells also include cells of the dermis, including vascular cells, lymph cells, cells of sweat and sebaceous glands, nerve cells, fibroblasts, and any other cell found in the various layers of the dermis including the papillary layer and the reticular layer. Skin cells also include those of the subcutis, i.e., the innermost layer of the skin, which includes fat and collagen cells.

The present invention encompasses delivery regimens where dsRNAs or nucleic acid vectors expressing the same are delivered to both skin cells and muscle cells simultaneously or sequentially. The means by which intradermal, subcutaneous, and/or intramuscular administration may be achieved includes needle injection, needleless injection, electroporation, biolistic approaches, and any other method that can accomplish delivery into a muscle or skin cell or a cell in muscle or skin tissue.

In one embodiment, the present invention encompasses methods of delivering nucleic acids, including double stranded RNA molecules and/or polynucleotide expression constructs encoding RNA molecules, e.g., mRNAs, antisense, ribozyme or dsRNA including RNAi agents such as siRNA, shRNA, or miRNA, to a target cell in vitro or ex vivo by delivering a nucleic acid to or expressing a nucleic acid in a cell that is competent for distal cell targeting. Competent donor cells may also be utilized for production in cell culture of RNA-containing exovesicles, or for autologous or heterologous transplant into a recipient mammalian organism. The cell may be a muscle cell, skin cell, stem cell, or any suitable competent cell. A cell which is competent for distal cell targeting may be obtained e.g., from a potential mammalian recipient, e.g., a human recipient, or from another donor, transfected in vitro or ex vivo with a selected polynucleotide expression construct or with selected RNA molecules, and implanted, e.g., subcutaneously or intramuscularly, into a recipient mammalian organism. The transplanted cell(s) may be autologous or heterologous with respect to the recipient. The recipient mammal may be an immunocompromised mammal or a mammal administered immunosuppressants. The implanted cells may then serve as a "factory" for in vivo production of RNA effector molecules, e.g., RNAi and/or mRNA molecules, for transport to a distal cell. Such cells may also express targeting ligands or other proteins enhancing exovesicle production, transport, targeting, and/or uptake, such as the receptor for HIV. The distal cell may be a liver cell such as a hepatocyte or another cell. The RNA effector molecule may repress a target gene in the liver, e.g., a gene of a pathogen such as a hepatitis virus or an endogenous disease-related gene found in the liver. The distal target cell may also be a non-liver cell, including any of the target cells described herein.

In one aspect, the invention relates to a method of dsRNA mediated gene inhibition or RNAi comprising delivering to muscle or skin cells of a mammal in vivo a nucleic acid expression vector encoding an RNAi or dsRNA agent. As described above, the RNAi agent(s) may be one or more hairpin or duplex dsRNA molecules, including one or more short hairpin dsRNA agents. The dsRNA expression vector may be DNA or RNA, including plasmid DNA. The expression vector may be a viral vector such as AAV for example. The polynucleotide expression vector may be supplied to the muscle as "naked" DNA or RNA (free from association with a transfection facilitating agent) or in association with an agent which facilitates transfection or transfer into mammalian skin cells or muscle cells or myocytes, including differentiated myocytes as well as undifferentiated myoblasts. In another aspect, the invention relates to such an RNAi method involving delivery by intramuscular electroporation-mediated transfection of skeletal muscle or myocytes, or skin cells of a mammal in vivo with a vector or construct expressing dsRNA molecules.

Numerous agents may be used to facilitate transfection of mammalian muscle cells in vivo including but not limited to polymer or peptide complexes, cationic amphiphiles, cationic lipids, cationic liposomic formulations, including the amino amide local anesthetic bupivacaine, particulates including gold particles utilized for biolistic or "gene gun" delivery, polycationic or cationic amphiphile agents including spermine and/or spermidine derivatives including various cholesteryl spermine compounds. The polynucleotide expression vector is frequently delivered to the mammalian muscle or skin tissue formulated in association with or as a complex with one or more of such transfection-facilitating agents.

Bupivacaine is one of the amphiphilic amino amide local anesthetic agents known to act as a transfection-facilitating agent for delivery into tissues including skeletal muscle of polynucleotide, including plasmid DNA, encoding immunogenic proteins, e.g., antigens of pathogens, for use in the field of DNA vaccines. The proteins are expressed in the muscle cells, triggering both humoral and cellular immune responses. See e.g., U.S. Pat. Nos. 6,217,900 and 6,383,512, "Vesicular Complexes and Methods of Making and Using the Same." Methods of injecting "naked" DNA encoding immunogenic and other biologically active polypeptides into muscle or skin are also known, see e.g., U.S. Pat. Nos. 5,580,859; 5,589,466. U.S. Pat. No. 6,413,942 describes delivering into muscle cells "naked" DNA encoding a secretable therapeutic polypeptide, e.g., growth hormone, which is released into the circulation to achieve a therapeutic effect. Among the numerous polycationic or cationic amphiphile compounds useful for facilitating transfection of polynucleotides in vivo in mammalian cells are various cholesteryl spermine or cholesteryl spermidine compounds including cholesteryl spermine carbamates and combinations thereof used as taught e.g. in U.S. Pat. Nos. 5,837,533; 6,127,170; 6,379,965; 5,650,096; and 5,783,565; and US 2006/0084617, published 20 Apr. 2006. These are just illustrative of the many chemically diverse agents known to those of skill in the art which may be employed to facilitate transfection of nucleic acids including dsRNA expression constructs into mammalian muscle or skin cells in accordance with the teaching of the invention.

Such naked and complexed nucleic acids may be used in delivery methods including needle and/or needleless injection directly into skin and/or muscle tissue, e.g., DNA expression vector complexed with 0.25% bupivacaine in a suitable vehicle for injection as taught above, as well as delivery to muscle or skin cells by the vascular route, such as the hydrodynamic method whereby increased intravascular pressure produces increased vascular permeability to the passage of molecules including nucleic acids into the interstitial space of muscle and skin tissue and increased uptake of such molecules by cells of the skin and muscle. Such increased intravascular pressure may be achieved through a combination of externally applied pressure e.g. tourniquet or cuff; and/or increased volume of drug administration; and/or increased speed of administration. Volumes administered to the limb of a mammal can be 250 ml, 500 ml, up to a liter or more. In one aspect, the nucleic acid is a DNA plasmid expression vector which can be administered in relatively large doses without toxicity, e.g. 100 mg, 200 mg, 350 mg, 500 mg to 1, 2, or 5 grams or more. Thus e.g. a delivery vehicle may be formulated comprising 350-500 mg naked or complexed DNA expression vector in 100 to 500 ml (e.g. 2 mg/ml) of citrate buffered 5% dextrose in water for injection (D5W). When administered rapidly into the afferent or efferent vascular system supplying a mammalian limb subjected to externally applied pressure, such a formulation provides a large amount of agent in the interstitial space of muscle cells, thereby facilitating transfection of cells by mass action. The formulation may be hypotonic, isotonic, or hypertonic. Administration of a hypertonic delivery vehicle may increase the transport of molecules such as DNA or other nucleic acids into adjacent muscle cells. See additional discussion below. Other delivery vehicles, excipients, and methods suitable for use in the methods of the invention may be formulated by those of skill in the art of pharmaceutical sciences, see e.g., the teaching of Remington's Pharmaceutical Sciences 18$^{th}$ Ed. (1990); Remington: The Science and Practice of Pharmacy, 20$^{th}$ Ed. (2000), 21$^{st}$ Ed. (2005). The teaching of all these cited references is incorporated herein by reference.

In another aspect, nucleic acids including dsRNA expression constructs are delivered into mammalian skin cells or striated or skeletal myocytes and/or myoblasts in vivo through electroporation. See, e.g., the formulations and methodology of electroporation of nucleic acid constructs into mammalian muscle cells as taught in US 2004/0014645 A1 "Increased delivery of a nucleic acid construct in vivo by the poly-L-glutamate ('PLG') system" and the methods and devices for electroporation taught in e.g., US 2005/0052630A1 "Constant current electroporation device and methods of use." See also US 2005/0070841A1 and US 2004/0059285A1 "Electroporation device and injection apparatus" and US 2004/0092907A1 "Method for muscle delivery of drugs, nucleic acids and other compounds." The various parameters including electric field strength required for electroporation of any known cell type including muscle and skin are generally known in the relevant research literature as well as numerous patents and applications in the field. See e.g., U.S. Pat. No. 6,678,556 "Electrical field therapy with reduced histopathological change in muscle"; U.S. Pat. No. 7,171,264 "Intradermal delivery of active agents by needle-free injection and electroporation"; and U.S. Pat. No. 7,173,116, which teaches formulations for gene delivery via electroporation, including formulations of various anionic polymers including poly-L-glutamate. Apparatus for therapeutic application of electroporation are available commercially, e.g., the Med-Pulser® DNA Electroporation Therapy System (Inovio/Genetronics, San Diego, Calif.), and are described in patents such as U.S. Pat. No. 6,567,694; U.S. Pat. No. 6,516,223, U.S. Pat. No. 5,993,434, U.S. Pat. No. 6,181,964, U.S. Pat. No. 6,241,701, and U.S. Pat. No. 6,233,482; electroporation may also be used for transfection of cells in vitro as described e.g. in US20070128708A1 Electroporation in vivo into mammalian muscle cells presents an attractive alternative for experimental applications as well as a promising delivery method for therapeutic applications in mammals including humans, with clinical trials underway in the DNA vaccines field. Electroporation may also be utilized to deliver nucleic acids into cells in vitro. Accordingly, electroporation-mediated administration into muscle and skin cells of nucleic acids including expression constructs utilizing any of the many available devices and electroporation systems known to those of skill in the art presents an exciting new means for delivering an RNA of interest to a distal target cell, tissue, or organ such as a hepatocyte or other liver cell.

In another embodiment, administration may be via needle injection, needleless injection, e.g., the Biojector® 2000 needleless injection device (Bioject Needle-free Injection Systems, Tualatin, Oreg.), which can be adjusted to deliver a liquid medication to various depths including intradermal, subcutaneous, and/or intramuscular. Other commercially available needleless injection systems include Dermo-jet (Robbins Instruments, Chatham, N.J.). Needleless injection relies on a high-pressure stream of the medication itself to penetrate the skin. As the fluid stream forces its way through the tissue, it follows the path of least resistance, resulting in a widely dispersed, spiderweb-like distribution of the medication. A transdermal patch might also be employed, as well as a biolistic injector or "gene gun" device capable of shooting a plasmid expression vector into cells, including cells in skin, the subcutaneous region, and/or muscle tissue. Biolistic or gene gun devices for in vivo delivery to mammals are commercially available, as e.g., the Helios Gene Gun (Bio-Rad, Hercules, Calif.) See, e.g., U.S. Pat. Nos. 5,830,877 and 6,723,077, which are herein incorporated by reference in their entireties.

In another aspect, intramuscular administration may be achieved through hydrodynamic intravascular methods which utilize various means, e.g., increased pressure, to promote delivery to cells including muscle, e.g., the Mims Pathway IV™ Gene Delivery methods (Mirus, Madison, Wis.) which utilize a cuff or tourniquet to restrict blood flow and increase pressure within the vessel in order to facilitate intravascular delivery of nucleic acids such as plasmid expression vectors to limb muscle. Any of a variety of methods known in the art may be used to increase the passage of a nucleic acid from afferent or efferent blood vessels into cells, including parenchymal cells of adjacent tissues. For example, increased vessel permeability to nucleic acids and other molecules may be achieved by the external application of pressure by a cuff such as a blood pressure cuff or tourniquet at a location distal to the site of nucleic acid administration and/or through increased intravascular pressure achieved by administering a selected pharmaceutical formulation in a relatively large injection volume and/or through rapid delivery and/or administration of biologically active agents such as papaverine, hyaluronidase, etc. The specific parameters for achieving optimal increases in vascular permeability in test subjects such as laboratory animals as well as human subjects are well within the level of skill in the arts of animal science, anatomy, physiology, pharmacology and clinical medicine. For example, optimal injection volume is related to the size of the animal to be injected as well as target tissue volume, e.g., volumes of 0.03 ml/g to 0.1 ml/g of body weight or greater may be required, with injection volumes of 70 to 200 ml reported for primates. Delivery to skeletal muscle tissue of a limb may be achieved by rapid intravascular injection or delivery through needle, catheter etc. of a relatively large volume (e.g., >5 ml per rat limb or >70 ml for a primate) with concomitant external application of pressure e.g. with a cuff or tourniquet, such that pressure within the vessel is increased and permeability to outward movement of oligonucleotide, polynucleotide, etc. is enhanced. See e.g., US 2004/0259828, U.S. Pat. No. 6,379,966; US 2007/0244067; Hagstrom et al., Molecular Therapy (2004) Vol. 10 (No. 2), 386-398; Herweijer and Wolff, Gene Therapy (2007) 14, 99-107; Lewis and Wolff, Advanced Drug Delivery Reviews 59 (2007) 115-123; the teaching of each of which is incorporated herein by reference. Such methods may be employed to deliver nucleic acids, including RNAs, DNAs, and mixtures thereof, to various parenchymal cells of tissues in a mammal, including cells of striated muscle as e.g., myoblasts, satellite cells, myotubules and myofibers, by delivery into an afferent or efferent blood vessel supplying the tissue, preferably a vessel of the arterial system such as an artery, arteriole, sinusoids, and/or capillary, but in some embodiments a vessel of the venous system, including a vein, venule and capillary. Increased transfection of such cells, including muscle cells, may be achieved e.g. by increasing the permeability of an afferent vessel proximal to the target tissue into which a selected nucleic acid is administered as taught e.g. in U.S. Pat. No. 7,148,205, "Intravascular delivery of non-viral nucleic acid". The nucleic acid, e.g., an RNA or a DNA expression vector, may be "naked" (i.e., free from agents which associate or complex with the nucleic acid and promote transfection) or associated or complexed with any one or more agents including amphipathic or amphiphilic compounds such as cationic amphiphiles, cholesterol and/or spermine containing complexes as described elsewhere herein. Various means may be used in order to increase vessel permeability, e.g., the naked or complexed nucleic acid may be supplied in a relatively large solution volume, and/or with physical measures to increase the pressure within the vessel by applying distal pressure and/or decreasing the vessel lumen, as e.g., with a tourniquet or cuff.

While some embodiments encompass transfecting skin cells or skeletal muscle cells or other competent cells in an animal with a nucleic acid encoding a dsRNA, methods wherein dsRNA is directly transfected into skin or muscle cells or other competent targeting cells are also encompassed. For instance, the invention includes a method of delivering at least one dsRNA to a target organ or tissue in an animal comprising transfecting skeletal skin or muscle cells or other competent targeting cells in said animal with said dsRNA, wherein said transfection results in said dsRNA being delivered to said other target organ or tissue.

Suitable dsRNA molecules for delivery to skin and muscle cells and other competent targeting cells include shRNAs and siRNAs for RNAi embodiments and are typically between about 15 to about 50 base pairs, and more particularly between about 19 and about 29 base pairs. The dsRNA and complexes or other formulations containing the same may be delivered to skin or muscle cells or other cells using any method known in the art, including those discussed above with regard to expression vectors.

Some dsRNA sequences, possibly in certain cell types and through certain delivery methods, may result in an interferon response. The methods of the invention may be performed so as not to trigger an interferon/PKR response, for instance by using shorter dsRNA molecules between 20 to 25 base pairs, by expressing dsRNA molecules intracellularly, or by using other methods known in the art. See US Application 20040152117, which is herein incorporated by reference. For instance, one of the components of an interferon response is the induction of the interferon-induced protein kinase PKR. To prevent an interferon response, interferon and PKR responses may be silenced in the transfected and target cells using a dsRNA species directed against the mRNAs that encode proteins involved in the response. Alternatively, interferon response promoters are silenced using dsRNA, or the expression of proteins or transcription factors that bind interferon response element (IRE) sequences is abolished using dsRNA or other known techniques.

By "under conditions that inhibit or prevent an interferon response or a dsRNA stress response" is meant conditions that prevent or inhibit one or more interferon responses or cellular RNA stress responses involving cell toxicity, cell death, an anti-proliferative response, or a decreased ability of a dsRNA to carry out a PTGS event. These responses include, but are not limited to, interferon induction (both Type 1 and Type II), induction of one or more interferon stimulated genes, PKR activation, 2'5'-OAS activation, and any downstream cellular and/or organismal sequelae that result from the activation/induction of one or more of these responses. By "organismal sequelae" is meant any effect(s) in a whole animal, organ, or more locally (e.g., at a site of injection) caused by the stress response. Exemplary manifestations include elevated cytokine production, local inflammation, and necrosis. Desirably the conditions that inhibit these responses are such that not more than about 95%, 90%, 80%, 75%, 60%, 40%, or 25%, and most desirably not more than about 10% of the cells undergo cell toxicity, cell death, or a decreased ability to carry out a PTGS event, compared to a cell not exposed to such interferon response inhibiting conditions, all other conditions being equal (e.g., same cell type, same transformation with the same dsRNA).

Apoptosis, interferon induction, 2'5' OAS activation/induction, PKR induction/activation, anti-proliferative responses, and cytopathic effects are all indicators for the RNA stress response pathway. Exemplary assays that can be used to measure the induction of an RNA stress response as described herein include a TUNEL assay to detect apoptotic cells, ELISA assays to detect the induction of alpha, beta and gamma interferon, ribosomal RNA fragmentation analysis to detect activation of 2'5' OAS, measurement of phosphorylated eIF2a as an indicator of PKR (protein kinase RNA inducible) activation, proliferation assays to detect changes in cellular proliferation, and microscopic analysis of cells to identify cellular cytopathic effects. See, e.g., US Application 20040152117, which is herein incorporated by reference.

As noted above, while not wishing to be bound by any particular mechanism, the present inventors have hypothesized that double-stranded RNA molecules transcribed from expression constructs in muscle and skin cells are delivered to the liver, possibly inside exovesicles formed from membrane blebbing or shedding at the surface of the transfected cell. In line with this hypothesis, the present invention also includes co-transfecting or co-expressing, along with an RNA of interest including dsRNA or therapeutic mRNA in muscle cells or other competent cells, genes encoding surface or transmembrane ligands specific for the target cell, organ or tissue of interest. Genes encoding targeting ligands may be expressed on the same vector as the dsRNA, for instance from a separate promoter, or may be expressed from a separate vector. In some embodiments, among others, the dsRNA is expressed from a polIII promoter and the targeting ligand is expressed from a polII promoter. Incorporation of such surface ligands into exovesicles could further enhance delivery to the liver, or facilitate delivery to other targets such as cancer cells or immune cells.

For instance, the present invention encompasses methods whereby skin or muscle cells or other competent targeting cells are transfected with (1) eiRNA or dsRNA or dsRNA complexes and (2) an expression vector encoding a cell-surface ligand that specifically binds to a receptor on the target cell. The eiRNA expression vector and the ligand-encoding expression vector may be a single expression vector or two different expression vectors. As an example, expressing a viral glycoprotein (such as the HIV envelope glycoprotein gp120) in muscle or skin cells in addition to HIV-targeting dsRNAs should lead to the formation of anti-HIV dsRNA-containing muscle exovesicles comprising HIV glycoprotein on the surface. These exovesicles now have the potential to be taken up by the T cells and other CD4+ immunocytes that HIV infects. Other suitable cell surface ligands and target cells include the influenza A hemaglutinin (HA) receptor binding domain which recognizes and interacts with an oligosaccharide on the surface of respiratory epithelial cells. Since avian influenza A viruses and human influenza A viruses preferentially target different epithelial cell-surface oligosaccharide receptors (e.g., epithelial cell receptors identified as glycans terminated by an $\alpha 2,3$-linked sialic acid (SA) that preferentially bind avian strains and glycans terminated by an $\alpha 2,6$-linked SA that bind human strains. *J. Virol.*, August 2006, p. 7469-7480, Vol. 80, No. 15), expression constructs can be designed to express dsRNAs active against human and/or avian influenza A viruses as well as influenza A receptor binding domains that preferentially target the human receptor and/or the avian receptor. Still other examples of cell surface ligands and target cells will be readily apparent to those of skill in the art of virology. For example, HBsAg can be encoded to further facilitate delivery to hepatocytes. Any viral receptor binding protein encoded by a virus can be expressed to target the blebs or exovesicles to cells infected by or capable of being infected by the respective viruses. Cells can be targeted prophylactically or therapeutically.

Any suitable cell surface ligand having specificity for a target cell surface receptor may be expressed in transfected cells, by cloning the gene for the cell surface ligand behind a promoter operable in the transfected cell such that the cell surface ligand is expressed and displayed on the surface of the transfected cell. In order to preferentially localize expressed cell surface ligands into exovesicles, the gene for the cell surface ligand may be fused to or be engineered to incorporate suitable targeting signals from proteins known to be incorporated into exovesicles at the surface of the transfected cell.

For example, as discussed above, galectin is one protein expressed at high levels in skeletal and smooth muscle cells, which has been observed to become specifically concentrated in plasma membrane evaginations and extruded in extracellular vesicles. Cooper and Barondes, 1990; Cooper, 1997; Harrison and Wilson, 1992. A variety of other galectin genes have been detected in different cell types, each lacking a signal sequence and containing a highly conserved core sequence of about 130 to 135 amino acids containing a carbohydrate recognition domain (CRD) between about residues 30 and 90. See Cooper and Barondes, 1999. Walter Nickel and colleagues have found that the CRD domain in galectin is necessary for export, suggesting that the galectin export machinery makes use of β-galactosidase-containing surface molecules as export receptors for intracellular galectin-1. Seelenmeyer et al., 2005. Accordingly, it may be possible to target other cell surface ligands to exovesicle evaginations in the cell membrane by fusing the coding regions for such cell surface ligands in frame to all or part of the galectin CRD domain coding region. The complete amino acid sequence of galectin-1 has been determined from human, as well as several other species including cow, rat, mouse, chicken and electric eel. Inagaki et al., 2000; Hirabayashi et al., 1988, Complete amino acid sequence of a β-galactosidase-binding lectin from human placenta, J. Biochem. (Tokyo) 104:1-4; Abbott and Feizi, 1989, Evidence that the 14 kDa soluble beta-galactosidase-binding lectin in man is encoded by a single gene, Biochem. J. 259: 291-94; Couraud et al., 1989, Molecular cloning, characterization, and expression of a human 14 kDa lectin, J. Biol. Chem. 264: 1310-16.

Galectin-3 is another member of the galectin family shown to be secreted by the pinching off of evaginating membrane domains and the release of extracellular vesicles where it is protected from proteolysis. Krzeslak and Lipinska, 2004. Electron microscopy has demonstrated that the vesicles are morphologically heterogenous and have a small size (up to about 0.5 microns). Galectin-3 is unique in the galectin family in possessing an extra N-terminal domain consisting of 100-150 amino acids depending on the species of origin, which has been proposed to contain targeting information for non-classical secretion. Further, at least one group has shown that the addition of this N-terminal segment to a normally cytosolic protein such as chloramphenicol acetyltransferase (CAT) resulted in efficient export of the fusion protein from transfected Cos cells. See Mehul and Hughes, 1997. Accordingly, it should be possible to target other cell surface ligands to exovesicle evaginations in the cell membrane by fusing the coding regions for such cell surface ligands in frame to all or part of the coding region for this galectin-3 N-terminal domain. Other classical methods of expressing targeting ligands on the cell surface may also be used.

The invention also encompasses methods wherein genes for cell surface receptors having binding specificity for cell surface ligands expressed in the competent cell are cloned, transfected into and expressed in target cells in vivo. Alternatively, recombinant genes may be introduced into target cells that upregulate expression of targeted cell surface receptors. Administering certain drugs to the patient may also result in the upregulation of target cell surface receptors depending on the target cell surface receptor of interest.

In some embodiments, the methods of the present invention may further comprise isolating at least one exovesicle from a transfected cell, wherein the isolated exovesicle contains the nucleic acid, for instance a dsRNA, and contacting said target cell with the isolated exovesicle. Exovesicle-producing cells may be transfected in vitro or in vivo, and dsRNA-containing exovesicles thereafter isolated and used to contact target cells. Methods for transfecting exovesicle-producing cells and cell lines in vitro with expression vectors and dsRNA compositions are known in the art, as are methods of isolating exovesicles. For example, Mehul and Hughes have disclosed a method of isolating a galectin-3-enriched vesicular fraction from murine macrophages and Cos-7 cells transfected with galectin-3 expressing plasmid. Mehul and Hughes, 1997, Plasma membrane targeting, vesicular budding, and release of galectin 3 from the cytoplasm of mammalian cells during secretion, J. Cell Sci. 110: 1169-78.

The methods of the present invention may be used in methods of treating and preventing diseases in mammals, particularly humans. Any mammal may be treated by the methods of the present invention, including but not limited to humans, primates, laboratory animals such as mice, rats, rabbits, guinea pigs, etc, farm animals such as cows, sheep, pigs, horses, goats, etc., as well as domestic animals including cats, dogs, etc. The experiments described herein show that diseases may be treated therapeutically or prophylactically. In particular, the present invention demonstrates that dsRNA expressed in or just below the skin, or in skeletal muscle may be delivered to other organs or tissues. Accordingly, the present invention may be used to treat or prevent any disease of an organ or tissue in which a reduction in gene expression is effective. For example, the invention includes a method of treating a patient suffering from an infection of an organ or tissue, for instance a viral infection, by delivering viral specific dsRNAs and dsRNA-containing viral drugs to the infected target cell.

In the case of hepatitis B and/or C viral infection, for example, HBV- and/or HCV-specific dsRNAs or other dsRNA-containing HBV- or HCV-specific drugs are delivered to the liver by intramuscular, intradermal or subcutaneous administration or by administration to any other competent targeting cell. Any HBV and/or HCV gene sequence may be targeted. Other liver viral diseases treatable by the methods of the present invention include CMV-induced hepatitis and HAV, HBV and/or HDV, and HEV and HAV.

In the case of HIV infection, for example, HIV-specific dsRNAs or other dsRNA-containing HIV specific drugs are delivered to T cells, T cell progenitors or other cells susceptible to HIV infection by intramuscular, intradermal or subcutaneous administration or by administration to any other competent targeting cell. Any suitable HIV gene sequence may be targeted, including but not limited to env (gp12), gag, and pol. As with any highly mutable virus, it is desirable to deliver a plurality of dsRNA molecules targeting two, three, four, five or more different HIV viral gene sequences and/or different HIV viral genes, e.g., one or more sequences from HIV env (gp120 and gp 41), HIV gag (p24, p17, etc.), and/or HIV pol (including protease, p31 integrase, p15 RNase, and p51 reverse transcriptase) which code for structural proteins, and/or one or more sequences from the HIV regulatory genes tat, rev, nef, vif, vpr and vpu, which code for proteins that control the ability of HIV to infect a cell, produce new copies of virus, or cause disease. In the case of HIV, as discussed above, expressing HIV gp120 glycoprotein in muscle cells or other competent cells in addition to HIV-targeted dsRNA should lead to the formation of dsRNA-containing exovesicles comprising HIV glycoprotein on the surface. These exovesicles now have the potential to be taken up by the T cells and other CD4+ immunocytes that HIV infects. Any other ligand that binds to a receptor on the surface of T cells could also be used to target dsRNA or therapeutic mRNAs to T cells.

Other viruses that may be targeted by the present invention include, but are not limited to, influenza, RSV, rabies, picornarirus, polio, coxsacchie, herpes simplex virus Type I and 2, St. Louis encephalitis, Epstein-Barr, myxoviruses, JC, coxsakieviruses B, togaviruses, measles, paramyxoviruses, echoviruses, bunyaviruses, cytomegaloviruses, varicellazoster, mumps, equine encephalitis, lymphocytic choriomeningitis, rhabdoviruses including rabies, simian virus 40, human polyoma virus, parvoviruses, papilloma viruses, primate adenoviruses, coronaviruses, retroviruses, Dengue, yellow fever, Japanese encephalitis virus, and/or BK, or any viruses of the species/family Astoviridae, Togaviridae, Flaviviridae, paramyxoviridae, arteriviruses, Rhabdoviridae, Filoviridae, orthomyxoviridae, bunyaviridae, arenaviridae, reoviridae, Birnaviridae, circoviridae, adenoviridae, Iridoviridae, Retrovirus, Herpesvirus, Hepadenovirus, Poxvirus, Parvovirus, Papillomavirus, and Papovavirus.

Prion RNA, e.g., mRNA, can also be targeted for repression.

Infections by other pathogens may also be treated or prevented using the methods of the present invention, including protozoa, bacteria, yeast, and fungal infections. For example, for intracellular parasites such as *Plasmodia*, pathogen-specific dsRNAs or other dsRNA-containing drugs effective against the pathogen may be delivered to cells susceptible to infection by intramuscular, intradermal or subcutaneous administration or by administration to any other competent targeting cell. The methods of the present invention are especially useful for treating hepatocyte infection by *Plasmodia* species by intramuscular, intradermal or subcutaneous administration and/or expression and delivery of Plasmodium-specific dsRNA to the liver.

As discussed above, the present inventors hypothesize that expressed dsRNAs in muscle and skin cells are delivered to distal organs or tissues after being incorporated into exovesicles at the transfected cell surface. This incorporation could be a passive mechanism based on the sheer numbers of expressed dsRNA molecules in the cell cytoplasm, where dsRNAs are captured as a result of a natural process and carried along in the vesicle. In this regard, as described above, the invention would encompass methods of delivering any nucleic acid or other cellular component expressed at sufficient levels so as to be incorporated into membrane exovesicles as they bleb from the cell surface, including mRNAs expressed from therapeutic genes, i.e., gene therapy.

The following examples are provided to describe and illustrate the present invention. As such, they should not be construed to limit the scope of the invention. Those in the art will well appreciate that many other embodiments also fall within the scope of the invention, as it is described hereinabove and in the claims.

Examples

As reported herein the present inventors have found that intramuscular delivery of DNA/Bupivacaine complexes, or intramuscular electroporation-mediated transfection of muscle cells with a vector or construct expressing dsRNA molecules, e.g, shRNA (RNAi) molecules, is surprisingly able to reduce the expression of target genes expressed in the liver. Several sets of experiments are described which have demonstrated gene silencing in mouse liver, mediated by an expressed interfering RNA (eiRNA) expression vector injected into the muscle. Experimental designs differ most significantly in the sequence of administration of the test material (therapeutic vs. prophylactic), and the end product that is being assayed to ascertain the level of gene silencing taking place. In the therapeutic model, the target molecule (plasmid expressing an RNA to be silenced) is administered before the drug molecule (plasmid expressing the shRNA silencing molecule) is administered. The reverse is true for the prophylactic model. In all experiments, the target RNA to be silenced is measured indirectly by quantitating the level of protein or enzymatic activity which is translated from the target RNA. In some experiments, the HBV surface antigen (sAg) is the measured end product. In others, luciferase activity is the measured end product.

In all the experiments described here, the hydrodynamic protocol used for injection of the target plasmid directs the plasmid to the liver, and is assayed at time points when the plasmid is expressed exclusively in the liver. In certain sets of experiments, expression of the target RNA is further restricted to the liver because a liver-specific promoter is used, which does not permit significant levels of transcription in other tissues. Since the liver secretes protein products into the circulatory system of the animal it is possible and convenient to sample the blood serum of the animal to measure the liver-based expression of the target plasmid in some of these experiments. Since obtaining a serum sample from the animal does not involve sacrificing the animal or otherwise disturbing liver function, this allows the investigator to repeatedly sample the target RNA levels in liver at multiple time points, indirectly by measuring the protein product or enzymatic activity of the indicator protein in the blood.

In all experiments "NUC050" refers to the eiRNA plasmid that is HBV-specific and which mediates sAg gene silencing. NUC049 is a negative control eiRNA plasmid (containing a mutated version of an shRNA derived from NUC050).

Example 1

Therapeutic Inhibition of HBV sAg Gene Expression In Vivo by Intramuscular Injection In the therapeutic model, animals receive exogenous RNA target in the form of a plasmid expressing the surface antigen coding sequence of HBV via hydrodynamic tail vein injection. Hydrodynamic injection is a method using a large volume with rapid injection time, to preferentially direct the DNA plasmid to the liver where it is expressed.

To obtain mice expressing a target gene in liver, HBsAg (surface antigen) cDNA was placed under the control of a liver-specific promoter in a commercially available plasmid vector (pLIVE). On Day −10, this vector was injected hydrodynamically into an immunodeficient strain of mice (NOD.CB17-Pkrdc$^{scid}$/J). In this way, DNA is largely localized to liver hepatocytes and the tissue-specific promoter further restricts expression of the sAg mRNA to these cells. Since the mice are immunodeficient, they are able to express the target gene for long periods of time (greater than a month) because immune response to the foreign protein encoded by the target gene will not be made.

Five days following target plasmid administration (Day −5), the mice were bled to determine levels of circulating HBsAg in serum.

On Day 0, mice were intramuscularly injected with the NUC050 vector at 1.0 mg/ml in a 0.25% bupivacaine solution in a total volume of 50 ul. The NUC050 vector encodes four different shRNA molecules which target various portions of the hepatitis B genome for degradation via the cellular RNAi mechanism. Three of these target the HBsAg regions contained in the target vector preadministered to the mice. A control group of mice was treated with the negative control NUC049 plasmid. (In some experiments, mice received another negative control plasmid, pGL2, which expresses luciferase mRNA but no shRNA molecules.)

Animals were subsequently bled again on Days 4, 11, 19, and 26 days post eiRNA vector administration, respectively, and levels of serum HBsAg were determined using an HBsAg ELISA commercially available (Bio-Rad, Hercules, Calif. HBsAg 3.0 EIA cat#. 32591). From 5 to 8 mice were used for each treatment group and the results are presented as HBsAg percent of initial HBsAg values (pre-treatment). The ability of the NUC050 vector treatment to decrease HBsAg expression was estimated by calculating, for each bleed day, a normalized difference value of average HBsAg levels for control minus experimental groups. Normalization was done by calculating the percent of HBsAg for each subsequent bleed day, relative to the HBsAg values on pretreatment. Wilcoxon statistical tests were used to assess the significance of the results. Experimental vs. control differences were taken to be significant at p-values less than 0.05.

Day 11 and Day 19 show statistically significant difference averages of –36% and –28% respectively, between NUC050 and NUC049 (p=0.0088, p=0.0339). (These values reflect underlying normalized average values of 56% and 93% prebleed (pretreatment) values for NUC050 and NUC049 respectively. For Day 11 the normalized average values compared to Prebleed values were 54% (NUC050) vs. 82% (NUC049) for Day 19.). Average values for all bleed days for NUC050 were substantially lower than all corresponding NUC049 values, but reached statistical significance on Days 11 and 19. See FIG. 1.

Example 2

Therapeutic Inhibition of HBV sAg Gene Expression In Vivo by Intramuscular Injection Mice (immunodeficient strain NOD.CB17-Pkrdc$^{scid}$/J) were given target HBV sAg (surface antigen) expression plasmid (directed to liver by hydrodynamic injection as described in Example 1) several days before being injected IM (intramuscularly) with 1) eiRNA vector expressing anti HBV shRNA, 2) negative control vector, or 3) left untreated after the initial injection of target plasmid. The eiRNA vectors for IM injection were formulated with 0.25% bupivacaine. Expression levels of the sAg, produced in the liver, were monitored by sAg ELISA of serum samples over the course of about 4 weeks.

In this model, sAg expression is expressed at a given level following injection, and then declines gradually over several weeks, if left simply to its own course, as seen in the mice left untreated after the initial target plasmid injection. By administering the eiRNA anti-sAg shRNA plasmid, the rate of decline of sAg increases over time relative to mice not treated after the injection of target HBsAg expression plasmid, or relative to mice given a negative control plasmid instead of the anti HBV eiRNA. An overall lower level of expression of sAg can also be observed in experimental vs. control groups of mice. Success rate and efficiency of muscle transfection by injection may be demonstrated by cotransfecting a reporter gene (e.g., by encoding a reporter gene such as EGFP on the eiRNA plasmids) and monitoring its expression either in whole muscle or tissue sections after injection.

Example 3

Prophylactic Inhibition of HBV sAg Gene Expression In Vivo by Intramuscular Injection Mice (immunocompetent strain C57Bl/6) were given a single intramuscular dose of the anti HBV shRNA effector plasmid, NUC050, or a negative control plasmid, which was followed three days later by hydrodynamic injection (via tail vein) of the target HBsAg plasmid (same target plasmid as in Exp 1 above). The control plasmid used in this experiment was the commercial vector pGL2, which encodes no protein and is used as an irrelevant plasmid control with respect to eiRNA activity. The IM injections were formulated with bupivacaine (0.25% w/v) with a DNA concentration of 1.0 mg/ml. 100 ul of the bupivacaine formulation was administered IM to each mouse (100 ug DNA).

Mice were bled for HBsAg ELISA assay at 3, 6, 9, and 13 days after the hydrodynamic administration of target plasmid.

Since the target plasmid encoding HBsAg mRNA and protein is given subsequent to the effector plasmid in the prophylactic model it is not possible to obtain a "baseline" sAg value for these mice prior to drug administration. Hydrodynamic injection is known to produce generally robust but highly variable levels of sAg in this type of animal model. Therefore, the sAg level determined at any time point reflects an unknown variation in the potentially maximal level of sAg expression from the target plasmid as well as the experimental variable of interest, which is the gene silencing effect of the eiRNA plasmid. For this reason, a comparison of the overall levels of sAg in the control and experimental groups is not conclusive, and a rate analysis (also called "slope" analysis") is performed.

The rate of decline of sAg levels between days 3 and 13 is approximated first by fitting a line to the data curve, and then comparing the slopes of this best fit line between control and experimental groups. The results revealed an increase in the decay rate of sAg mediated by the NUC050 eiRNA plasmid, relative to negative control plasmid or mice given only the target plasmid. The rates of decrease range from 1.4 to 1.7 times greater for eiRNA treatment compared to control mice.

Example 4

Prophylactic Model Using Immunodeficient Strain NOD.CB17-Pkrdc$^{scid}$/J, Multiple Dosing and Luciferase Readout In this experiment, using bupivacaine formulations only, of the NUC050 (eiRNA against HBV sAg) and the NUC049 (negative control) vectors, a dual reporter system was used to normalize for the liver-directed expression of target plasmid.

The target plasmid contains two separate genes encoding luciferases from two different organisms, firefly (FF) and jellyfish (Renilla or "JF"). See WO 04076629A3: Methods and constructs for evaluation of mai targets and effector molecules. Because each produces a different wavelength of luminescence upon hydrolysis of luciferin substrate, the two signals can be measured in the same sample. The renilla luciferase mRNA is engineered as a fusion mRNA with sequence elements present in the HBV genome, such that the fusion mRNA becomes a target for the NUC050 eiRNA plasmid, and the signal from renilla is a measure of the gene silencing effect of NUC050. Activity of NUC050 will therefore result in a reduction of the renilla luciferase signal even though it targets HBV sequences because the HBV sequences are present at the end of the renilla mRNA. The FF luciferase signal serves as a normalization standard to correct for overall variability in target plasmid delivery/transfection, because it is not subject to down modulation by the eiRNA effector, but is dependent on the same plasmid for expression. Thus, taking the ratio, JF:FF luciferase normalizes for the liver-directed expression of plasmid. In cases where an insufficient FF luciferase is observed, it can be concluded that the plasmid was not delivered, and therefore the sample is not valid for analysis.

In this experiment, 25 animals were used for each treatment group. Levels of FF luciferase were acceptable for 19/25 animals in the eiRNA (NUC050) group and for 17/25 animals in the control (NUC049) group. A box-and-whisker plot diagram of all ratio values indicates a clear shift to lower renilla: FF ratios in the treatment vs. the control group as expected from the silencing effect of the NUC050 plasmid.

Because the average FF luciferase signals were higher in the NUC050 vs. the NUC049 group, data were also analyzed by comparing the renilla:FF ratios in subgroups of animals with similar levels of FF luciferase expression in both treatment groups. In the top or highest subgroup (most firefly luciferase) the ratio shift went from 33.5 for the control NUC049 mice to 24.8 for the NUC050 mice (26%). Thus, there was a 26% reduction in the renilla:FF ratio in the subgroup of animals expressing the highest amount of firefly luciferase. There were a total of 10 mice in this group. The next highest subgroup showed an 8% difference and went from a ratio of 30.8 to 28.4. There were only 5 mice in this group or bucket. The remainder of the mice were in lower expressing groups with lesser differences between the groups as expected but still some differences existed. The overall difference between the 2 groups comparing all animals was 10%.

To assess the significance in the 10-26% reduction in renilla:FF ratio seen across groups and subgroups, we compared the reduction in ratio to that in animals receiving both the target and effector plasmids together by direct hydrodynamic delivery. Direct hydrodynamic delivery of both target and effector plasmids typically resulted in a maximal 30% silencing effect in this system. Therefore, as compared to a 30% maximal effect, the 10-26% seen with this novel delivery mechanism appears quite significant and suggests that these experiments can serve as a basis for novel methods and compositions for eiRNA and siRNA/shRNA mediated gene silencing via muscle delivery.

Example 5

In Vivo Electroporation Delivery of eiRNA: Dual Luciferase Model

To test whether in vivo electroporation would be an efficient way to deliver eiRNA into skeletal muscle cells, the mice were first anesthetized, the IM injection given and the electrodes placed into the muscle and the pulses are delivered. More specifically, C57Bl/6 female were given an intramuscular (IM) injection in the tibialis muscle of one leg of either NUC 050 (drug substance) or NUC 049 (negative control) formulation at a volume of 25 uL, concentration of 2.0 mg/ml. We used a 3-pronged probe from Advisys, The Woodlands, Tex., and placed it on the tibialis muscle of the mouse leg. Two pulses of electricity were administered (see details in table below).

TABLE 1

| Electroporator settings | | |
|---|---|---|
| Pulse In Sequence: | 1 | 2 |
| Prewait (s): | 4 | 1 |
| Pulse Width (ms): | 52 | 52 |
| Pulse Current (A): | 0.1 | 0.1 |

Six days after dosing, all mice were given a hydrodynamic injection, or "challenge," of 1 ug of the expression plasmid (NUC 060, dual-luciferase HBV-fusion plasmid).

Five days after the hydrodynamic injection, all mice were sacrificed and their livers were dissected, frozen, and stored at −70 C. Livers were homogenized with a mechanical homogenizer in a cell lysis buffer, centrifuged, and the supernatant was removed for analysis. Supernatant samples from all livers were assayed for the presence of both Renilla and firefly luciferase proteins. The ratio of Renilla:firefly luciferase (RLU) represents a normalized expression profile and serves as the output measure of the assay. The mean Renilla:firefly luciferase ratio of the NUC 050 group is compared to the mean ratio of the NUC 049 group. This difference is represented as a net ratio value and a percent difference:

$$\frac{\%}{\text{Difference}} = \frac{\text{Mean } NUC\ 050 - \text{Mean } NUC\ 049}{\text{Mean } NUC\ 049} \times 100\%$$

The difference of the two means is tested for statistical significance using a nonparametric 2-sample Wilcoxon test for a p-value less than 0.05.

Figure 2:
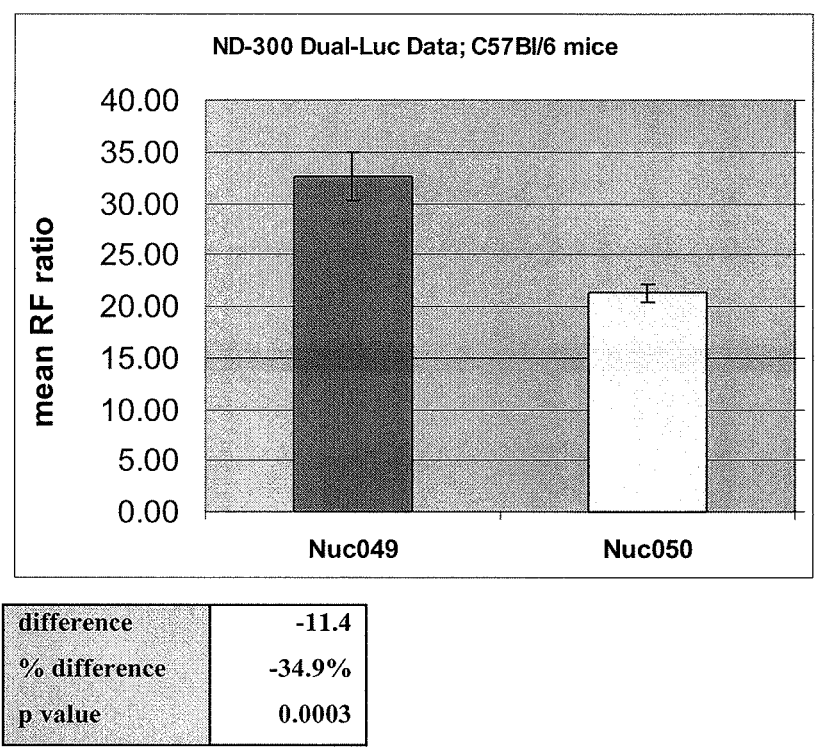
FIG. 2. Graph showing the ratio of Renilla:firefly luciferase (RLU) in response to muscle electroporation of NUC050 versus NUC049 in C57Bl/6 mice. Mice were administered either NUC050 plasmid or negative control plasmid NUC049 via intramuscular (IM) injection concomitantly with electroporation (EP) at day 0. On day 6, both groups of mice received a hydrodynamic injection (HDI) of the dual-luciferase reporter plasmid NUC060. Values represent the mean Renilla RLU/Firefly RLU ratio for each group of animals. The 34.9% difference is statistically significant by non-parametric Wilcoxon two-sample test ($p<0.05$).
Figure 3:
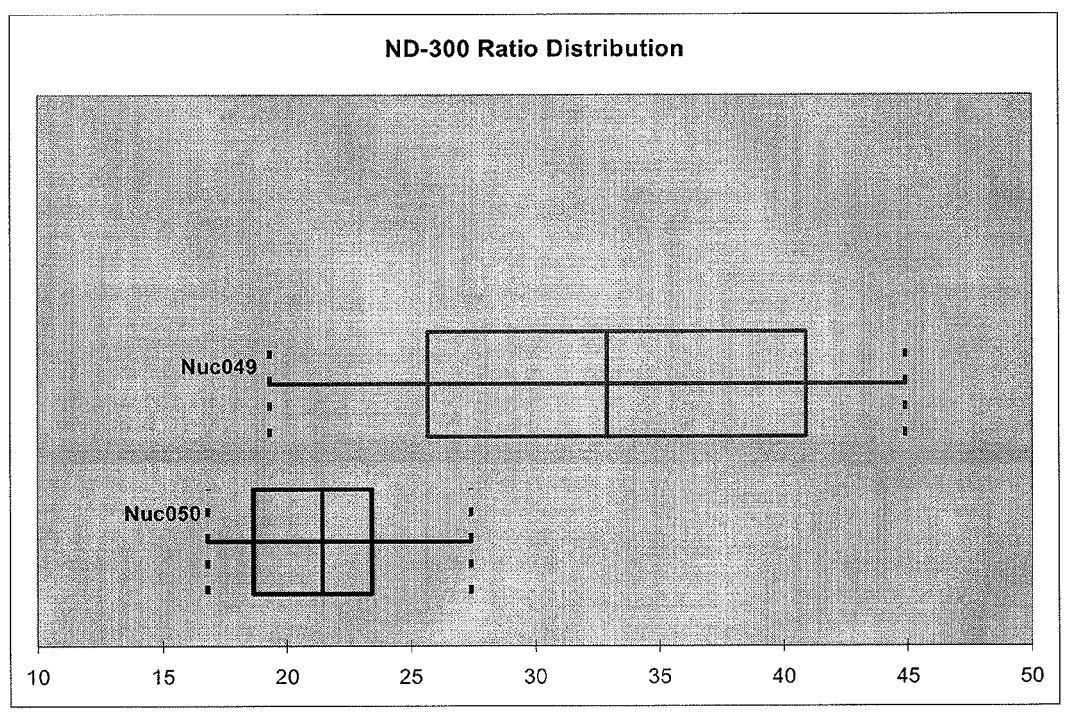
FIG. 3. Box-and-whisker plot of individual mouse ND-300 ratios for NUC050 versus NUC049. The distribution of Renilla:Firefly ratio values among individual animals in each respective group can be visualized by the box- and whisker plot. The 'box' portion represents the interquartile range (Q1-Q3). The vertical line within the box represents the median average.

The results indicate a 35% reduction in the fusion Renilla mRNA with respect to the Firefly mRNA in the NUC050 group (See FIGS. 2 and 3 and Tables 2 and 3). With respect to the results obtained with IM injection (non-electroporation) of NUC050, these results are consistent with the better muscle transfection when electroporation is used as the means for transfecting muscle with the eiRNA vectors. This is also consistent with a liver delivery rate of siRNAs or shRNAs to hepatocytes approximating and perhaps exceeding what is typically achieved by hydrodynamic injection when the eiRNA is hydrodynamically injected first and then the dual luciferase vector challenge is given by hydrodynamic injection (HDI) later. We estimate based on this data that about 40%-60% of hepatocytes have likely picked up one or more shRNAs encoded by NUC050. This is because each hydro injection typically transfects about 40-60% of hepatocytes. Transfection of hepatocytes following HDI is random and the second HDI would hit about 40-60% of the cells that were transfected by the first HDI.

TABLE 2

| Individual Mouse Values (ratios) | | |
|---|---|---|
| # | 300-1 Nuc050 | 300-2 Nuc049 |
| 1 | 16.8 | 19.3 |
| 2 | 17.7 | 22.4 |
| 3 | 18.6 | 25.4 |
| 4 | 18.7 | 26.0 |
| 5 | 20.0 | 26.1 |
| 6 | 20.6 | 30.8 |
| 7 | 21.4 | 32.9 |
| 8 | 21.8 | 34.9 |
| 9 | 23.2 | 36.6 |
| 10 | 23.3 | 39.7 |

TABLE 2-continued

Individual Mouse Values (ratios)

| # | 300-1 Nuc050 | 300-2 Nuc049 |
|---|---|---|
| 11 | 23.5 | 42.1 |
| 12 | 23.7 | 44.0 |
| 13 | 27.4 | 44.9 |
| Mean | 21.3 | 32.7 |
| Sd | 2.97 | 8.49 |

TABLE 3

Additional Analysis

| | Nuc050 | Nuc049 |
|---|---|---|
| Mean | 21.28 | 32.69 |
| Standard Error | 0.82 | 2.35 |
| Median | 21.43 | 32.90 |
| Mode | #N/A | #N/A |
| Standard Deviation | 2.97 | 8.49 |
| Sample Variance | 8.84 | 72.01 |
| Kurtosis | −0.09 | −1.30 |
| Skewness | 0.34 | 0.00 |
| Range | 10.62 | 25.60 |
| Minimum | 16.78 | 19.30 |
| Maximum | 27.40 | 44.90 |
| Sum | 276.70 | 425.01 |
| Count | 13 | 13 |

Example 6

In Vivo Electroporation Delivery of eiRNA Against HBV Surface Antigen

In this experiment, immunocompetent C57Bl6 mice were electroporated intramuscularly with the anti-HBV eiRNA (NUC050) or with an irrelevant eiRNA (NUC049). Following electroporation, shRNAs encoded by the eiRNA vectors are transcribed to high copy levels in the electroporated muscle (2,000,000,000 copies of individual shRNA detected by QRT-PCR in piece of electroporated muscle). Seven days post intramuscular electroporation (IM-EP), groups of mice were challenged by hydrodynamic injection with three different doses of NUC054, an HBV expression vector encoding HBsAg. The doses were 10 ug, 5.0 ug and 2.0 ug NUC054. The hydrodynamic injections also all contained identical amounts of a hAAT expression vector as a marker for successful HDI, i.e., serum hAAT values are a surrogate marker of the amount of NUC054 transfection since both plasmids were co-administered. The total amount of DNA was kept constant in each injection through the inclusion of an inert filler plasmid, pGL2-basic.

Two days, seven days and 16 days following challenge with NUC054, blood was collected from mice for measurement of HBsAg. If IM-EP of NUC050 is specifically able to downregulate serum HBsAg (as compared to the control NUC049), then transfected muscle must be able to relay plasmid specified molecules such as shRNA/siRNA produced in the muscle to hepatocytes where RNAi of the HBV target mRNA occurs. This is because NUC054 which encodes the HBV mRNA is expressed in hepatocytes specifically following HDI of NUC054 and if downregulation occurs, it must occur in hepatocytes. HBsAg is made in hepatocytes and is secreted into serum where it can be measured. As discussed further below, the results indicate that NUC050 specifically and with statistical significance downregulates the expression of HBsAg in mice that were given NUC050 via intramuscular electroporation.

Statistical Analysis

The serum surface antigen (sAg) concentrations 2 days post challenge from mice that received NUC050 plasmid treatment and 2, 5 or 10 ug of hydrodynamically injected sAg plasmid (NUC054) were compared to the group comprised of serum sAg concentrations on the same day from mice that received the control treatment NUC049 plasmid and either 2, 5, or 10 ug of hydrodynamically injected NUC054 using a Wilcoxon two-sample one-sided test application provided by Dr. Sam Litwin. The NUC050 treatment resulted in statistically significantly lower serum sAg values compared to those from the control group (p=0.005).

The analysis above was performed for data obtained 7 days post challenge and the NUC050 treatment resulted in statistically significantly lower serum sAg values when compared to the control group (p=0.002).

The serum hAAT values from mice that received NUC050 treatment and 2, 5 or 10 ug of hydrodynamically injected sAg plasmid were matched with hAAT values from mice that received the control NUC049 treatment and 2, 5 or 10 ug of hydrodynamically injected NUC054 plasmid. Serum hAAT values are a surrogate marker of the amount of NUC054 transfection since both plasmids were co-administered. Data from unmatched animal pairs was not used. The day 2 sAg concentrations from mice that received NUC050 plasmid treatment were compared to the matched group comprised of sAg concentrations on the same day from mice that received the control treatment NUC049 plasmid using a Wilcoxon paired-sample one-sided test application provided by Dr. Sam Litwin. The results of the test showed that the NUC050 treatment resulted in statistically significantly lower sAg concentrations compared to the control group (p=0.011).

The serum hAAT values from mice that received NUC050 treatment and 10 ug of hydrodynamically injected sAg plasmid were matched with hAAT values from mice that received the control NUC049 treatment and 10 ug of hydrodynamically injected NUC054 plasmid. Serum hAAT values are a surrogate marker of the amount of sAg transfection since both plasmids were co-administered. Data from unmatched animal pairs was not used. The sAg concentrations on day 2 from mice that received NUC050 plasmid treatment were compared to the matched group comprised of sAg concentrations on the same day from mice that received the control treatment NUC049 plasmid using a Wilcoxon paired-sample one-sided test application provided by Dr. Sam Litwin. The results of the test showed that the NUC050 treatment resulted in sAg concentrations that were statistically significantly (p=0.009) less than those from the control NUC049 plasmid group. See Table 4.

TABLE 4

| Sample | Test | p-value |
|---|---|---|
| Combined day 2 data | Wilcoxon 2 sample | 0.005 |
| Combined day 7 data | Wilcoxon 2 sample | 0.002 |
| Combined day 2 data matched | Wilcoxon paired | 0.011 |
| 10-ug day 2 data matched | Wilcoxon paired | 0.009 |

Example 7

Quantitation of siRNA Expressed in Muscle

The purpose of this experiment was to measure the amount of siRNA expressed in muscle from an eiRNA plasmid following intramuscular electroporation. For our hypothesis of transfected muscle cell to act as a depot to deliver siRNA/shRNA or DNA to distal sites, the muscle must first be transfected. If muscle is secreting or exporting vesicles containing siRNA/shRNA, then the more of these molecules that are expressed, the more siRNA/shRNA will be shipped out of the cell, and a higher delivery to distal sites is expected.

In this experiment, mice were electroporated intramuscularly with NUC050. NUC050 expresses four HBV-specific shRNAs that are processed into siRNAs. For this experiment, only one of the siRNAs encoded was measured. Following electroporation, the area of muscle electroporated was harvested and snap frozen. RNA was subsequently extracted and one of the siRNAs expressed from NUC050, si1737, was measured by QRT-PCR.

QRT-PCR for detection of expressed siRNA's targeting HBV including si1737, si1907 and si2791 was performed utilizing the protocol described by Caifu Chen, et al. in (Chen Caifu/ABI Method: Nucleic Acid Research, 2005, 33(20): e179). Si1737 served as an example of the protocol. The procedure involves a reverse-transcription reaction to gener- The sequences of si1737 (underlined strands) and its loop primer are listed below:

```
                                              (SEQ ID NO: 1)
5'-GGAUUCAGCGCCGACGGGACG-3'

(SEQ ID NO: 2)
3'-TGCCCTGCGAGTTG-ACTTAACGGCTGAGGTGCTGTGGTCAACT
C-5'
```

After RT reaction, a cDNA as following will be synthesized:

```
                                              (SEQ ID NO: 3)
   3'-CCTAAGTCGCGGCTGCCCTGCGAGTTG-ACTTAACGGCTGAGGT
   GCTGTGGTCAACTC-5'
```

In Q-PCR reaction, higher concentration of forward primer (pink strand) preferentially makes more antisense cDNA (the blue strand):

```
5' CAGCTGGGA-GGATTCAGCGCCGAC-3' (SEQ ID NO: 4)
         3'-CCTAAGTCGCGGCTGCCCTGCGAGTTG-ACTTAACGGCTGAGGTGCTGTGGTCAACTC-5' (SEQ ID NO: 5)
```

Figure 4:
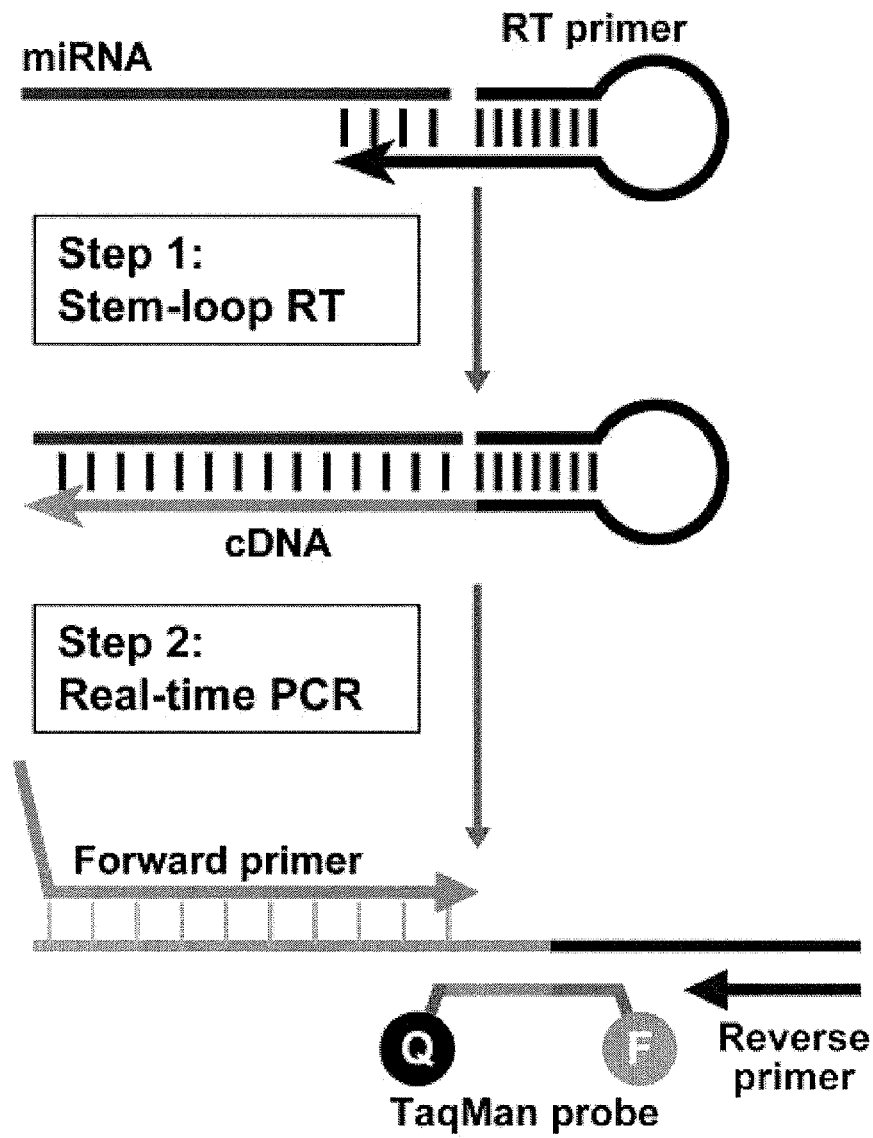
FIG. 4. Schematic description of TaqMan RNA assays, TaqMan-based real-time quantification of siRNAs includes two steps, stem-loop RT and real-time PCR. Stem-loop RT primers bind to the 3' portion of miRNA molecules and are reverse transcribed with reverse transcriptase. Then, the RT product is quantified using conventional TaqMan PCR that includes miRNA-specific forward primer, reverse primer and dye-labeled TaqMan probes. The purpose of tailed forward primer at 5' is to increase its melting temperature (Tm) depending on the sequence composition of miRNA molecules.

```
5' CAGCTGGGA-GGATTCAGCGCCGACGGGACGCTCAAC-TGAATTGCCGACTCCACGACACCAGTTGAG-3' (SEQ ID NO: 65)
``` ate cDNA from the siRNA. This is done primarily by the use of a loop primer, which matches 8 nucleotides of the siRNA sequence of 1737. (FIG. 4) This protocol utilizes a stem-loop primer for generating the cDNA for PCR from expressed siRNA. This method was shown to provide better RT specificity and efficiency than linear primers due to the base stacking of the stem of the primer, which enhances the thermal stability of the resulting RNA-DNA heteroduplex. The spatial constraint of the loop primer also improves assay specificity compared to linear primers as shown by Chen.

RNA for reactions was collected by the Invitrogen Trizol protocol (cat #15596-026). RNA from muscle tissue was extracted in Trizol using homogenization. The RT reaction was done in a 15 ul reaction volume with final concentrations of 10 mM $MgCl_2$, 1× GeneAmp PCR buffer (Applied Biosystems cat. #N808-0010), 50 nM loop primer, 0.26 mM dNTP, 3.33 U/µl MultiScribe Reverse Transcriptase (Applied Biosystems cat #4319983), 0.26 U/µl GeneAmp RNase Inhibitor (Applied Biosystems cat.#N808-0119). Reactions were incubated in an MJ Research PTC-200 Peltier Thermal Cycler for 30 min at 16° C., 30 min at 42° C. and 5 min at 85° C. The cDNA was then added to the Q-PCR reaction with a higher concentration of the forward primer. The excess forward primer preferentially binds and generates more antisense cDNA. The FAM probe for Q-PCR then binds the antisense cDNA along with the reverse primer, thus starting the Q-PCR detection. The Q-PCR reaction was done in 20 µl reaction volume with 2 µl of RT product input, and final concentrations of 1× Taqman Universal Master Mix No Amperase UNG (Applied Biosystems cat #4324018), 1500 nM forward primer, 750 nM reverse primer, 200 nM FAM probe. Reactions were run in an Applied Biosystems Real-Time PCR System 7300 for 40 cycles of 95° C. for 15 sec and 60° C. for 1 min using a FAM detector. Primer and probe sequences were as follows:

The antisense cDNA will be used for probe and reverse primer binding:

```
                                              (SEQ ID NO: 7)
5' CAGCTGGGA-GGATTCAGCGCCGAC-3'

(SEQ ID NO: 8)
5' CAGCTGGGA-GGATTCAGCGCCGACGGGACGCTCAAC-TGAATT
GCCGACTCCACGACACCAGTTGAG-3'

(SEQ ID NO: 9)
Q-TGCCCTGCGAGTTG-ACTT-Fam (SEQ ID NO: 10)
3'-CTGAGGTGCTGTGGTCAACT-5'
```

Si1737 chemically synthesized by IDT, Ames Iowa was used to generate a standard curve and for use in spike recovery.

All four electroporated muscles from study ND311 that were injected with NUC050 and APL050 showed expression levels of si1737 between 8.0 e+006 to 22 e+009 siRNAs. Electroporated muscles injected with the sAg expression vector alone, APL050, did not yield any detection of siRNA as we predicted. Naïve muscle was also negative for siRNA expression as predicted. For results, see Table 5 below.

TABLE 5

| sample name | Detector | Task | Ct | quantity |
|---|---|---|---|---|
| 6.00E+08 | 1737 | Standard | 12.93 | 6.00E+08 |
| 6.00E+07 | 1737 | Standard | 15.55 | 6.00E+07 |
| 6.00E+06 | 1737 | Standard | 19.52 | 6.00E+06 |
| 6.00E+05 | 1737 | Standard | 22.51 | 6.00E+05 |
| 6.00E+04 | 1737 | Standard | 26.05 | 6.00E+04 |
| ND311 APL050 1A muscle | 1737 | Unknown | undet. | |
| ND311 APL050 1B muscle | 1737 | Unknown | undet. | |

TABLE 5-continued

| sample name | Detector | Task | Ct | quantity |
|---|---|---|---|---|
| ND311 APL050 1C muscle | 1737 | Unknown | undet. | |
| ND311 APL050 1D muscle | 1737 | Unknown | undet. | |
| ND311 ALP050 + Nuc050 2A muscle | 1737 | Unknown | 19.04 | 7.24E+06 |
| ND311 ALP050 + Nuc050 2B muscle | 1737 | Unknown | 19.88 | 4.04E+06 |
| ND311 ALP050 + Nuc050 2C muscle | 1737 | Unknown | 14.95 | 1.24E+08 |
| ND311 ALP050 + Nuc050 2D muscle | 1737 | Unknown | 15.97 | 6.10E+07 |
| Naïve muscle | 1737 | Unknown | undet. | |
| Negative control H2O | 1737 | Unknown | undet. | |
| Negative control H2O | 1737 | Unknown | undet. | |

Note 1.
RNA extracted from muscle was resuspended in a total volume of 12 ul. 5 ul of this extract was added to the initial RT reaction of which the total volume was 15 ul. 2u/l/15ul of the RT-reaction was used for a PCR reaction. This means the PCR values for siRNA copy number were multipled by 18 to get the copy number of si1737 in the muscle extracts. For example, the results obtained and displayed as data in the above table were multiplied by 18 to get the total copy number of si1737 in the extracted muscle sample.

Example 8

Electron Micrographs of Muscle Blebs

Figure 5:
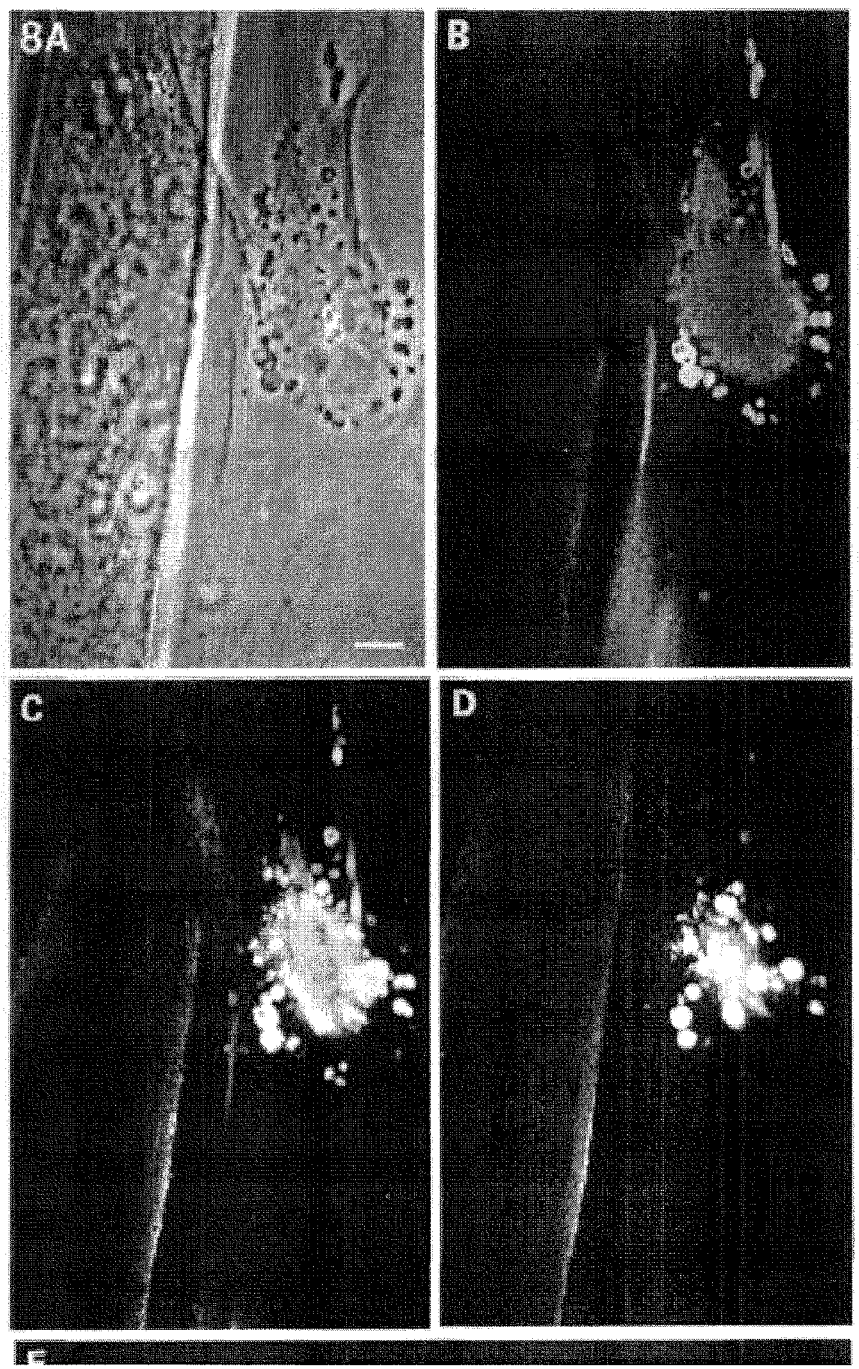
FIG. 5. Photos of published muscle blebs stained immunologically for β-galectin (FIG. 5, panels B, C and D) compared with a time lapsed photo by the present inventors of a myoblast secreting blebs (panel A).
Figure 6:
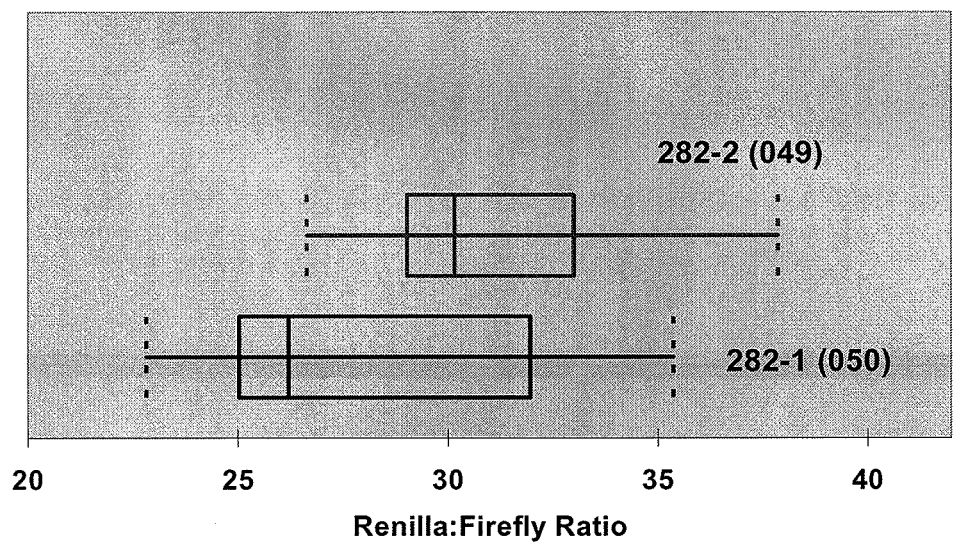
FIG. 6. Box-and-whisker plot showing the distribution of Renilla:Firefly ratio values among individual animals in each respective group can be visualized by the box- and whisker plot. The 'box' portion represents the interquartile range (Q1-Q3). The vertical line within the box represents the median average.
Figure 7:
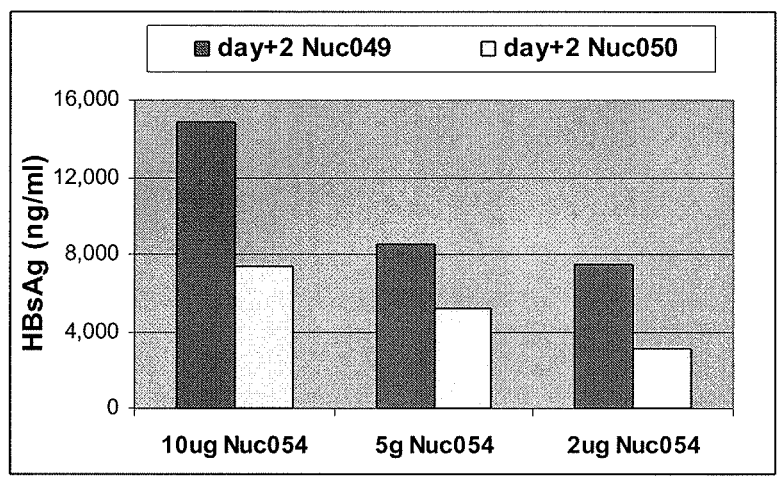
FIG. 7. Graph showing HBsAg Mean Values following intramuscular electroporation of NUC050 plasmid. The mean sAg levels of the three dose groups (10 ug, 5 ug, and 2 ug) are represented in graph (A) day +2, (B) day+7, and (C) day+16. The reduction in sAg in the NUC050 group is significant ($p<0.05$) in the day+2 10 ug group, the day+7 10 ug group, and the day+7 5 ug group.
Figure 7:
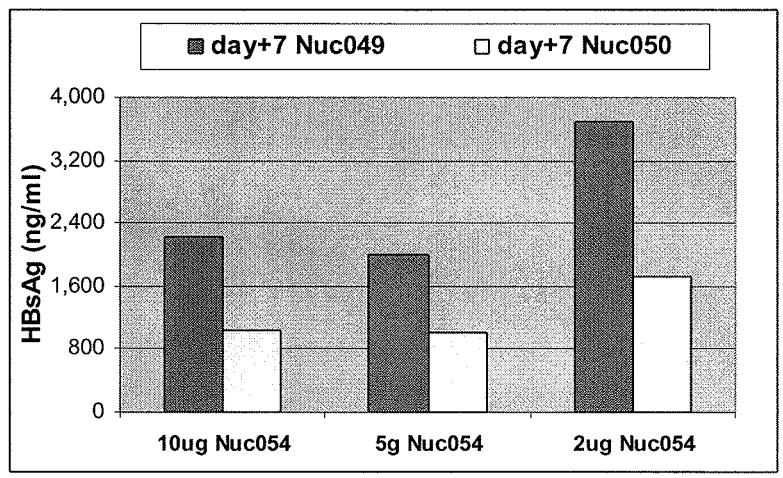
Figure 7:
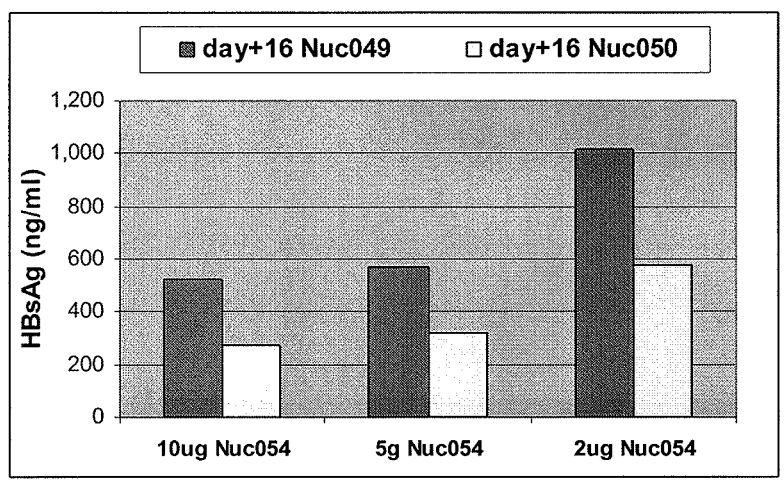

Photos of published muscle blebs stained immunologically for β-galectin (FIG. 5, panels B, C and D) were compared with a time lapsed photo by the present inventors of a myoblast secreting blebs (panel A). Prior to taking the picture, L6 cells (which contain myoblasts in culture that differentiate into myotubes) were transfected with an EGFP expression plasmid to see if we could see blebs and if so, whether they contain EGFP. If so, this indicates that blebs pack up cytosolic content into their interior. The picture in FIG. 5, panel A shows transfected myoblasts with bleb like structures that are fluorescent.

Example 9

Prophylactic Inhibition of HBV sAg Gene Expression In Vivo by Intramuscular Injection This example shows that subcutaneous injection of an eiRNA plasmid expressing siRNAs specific for Hepatitis B causing the distal downregulation of mRNAs containing Hepatitis B target sequences in liver hepatocytes. The results of the data would indicate that subcutaneous injection of eiRNA molecules/siRNA molecules and likely intradermal injection as well can mediate the downregulation of gene(s) in hepatocytes, not limited to the HBV sAg gene exemplified here. The molecules transferred to distal sites could be siRNA/shRNA, the eiRNA plasmid DNA or the RNA charged RNA Induced Silencing Complex. Any siRNA/shRNA and/or DNA would therefore be predicted to transfer. Although this model is prophylactic, since these results show that the active agent is transferring to hepatocytes, a therapeutic subcutaneous injection is also predicted to work.
Experiment Background
In the prophylactic model, the drug molecule (plasmid expressing the shRNA silencing molecule) is administered before the target molecule (plasmid expressing an RNA to be silenced) is administered.

Figure 9:
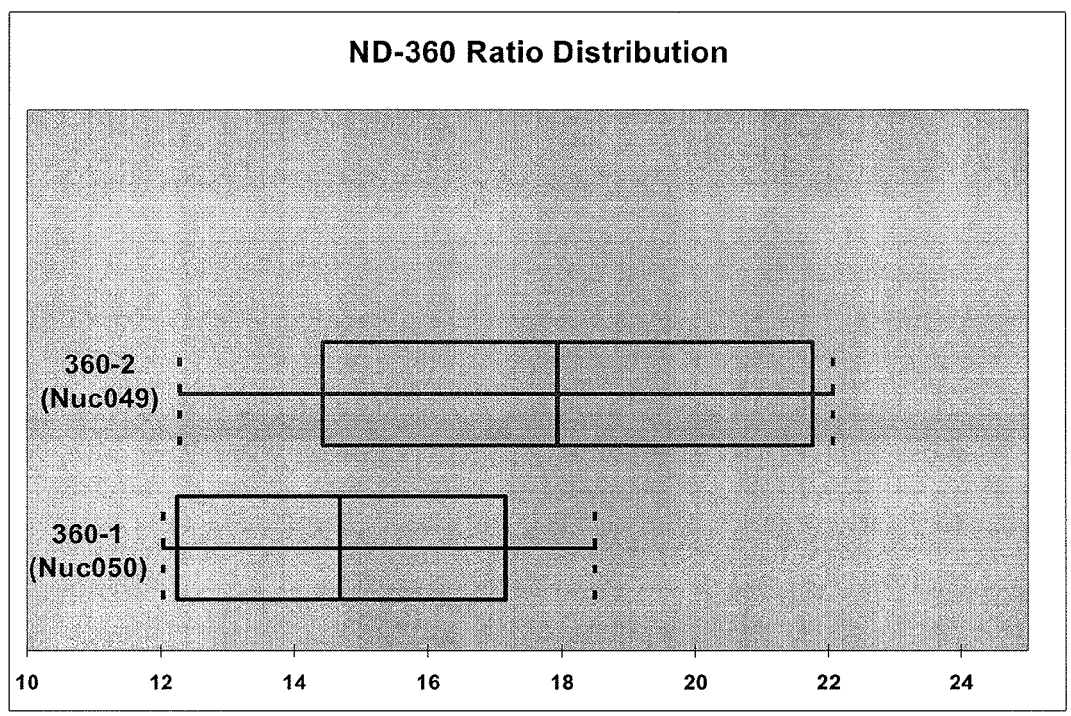
FIG. 9. Distribution of the individual mouse ND-360 ratios of Renilla/Firefly Luciferase activity for NUC050 versus NUC049. The distribution of Renilla:Firefly activity ratios among individual animals in the experimental (NUC050) and control (NUC049) groups of ND-360 is shown by the box-and whisker plot. The 'box' portion represents the interquartile range (Q1-Q3). The vertical line within the box represents the median and the horizontal lines extend to the lower and upper extremes of the distribution.

In all experiments "NUC050" refers to an eiRNA plasmid expression vector that expresses four different short hairpin dsRNAs (shRNAs) specific to HBV (see e.g., WO 2006/033756, plasmid pHB4, FIG. 9), which mediates silencing of an HBV-Luciferase fusion vector, "NUC060", e.g., as described in WO 04076629/US 2006/0263764. "NUC049" is a negative control eiRNA plasmid (which expresses a mutated version of a single shRNA derived from NUC050).

The target plasmid contains two separate genes encoding luciferases from two different organisms, Firefly (FF) and jellyfish (Renilla or "JF"). See WO 04076629: Methods and constructs for evaluation of RNAi targets and effector molecules. Because each produces a different wavelength of luminescence upon hydrolysis of luciferin substrate, the two signals can be measured in the same sample. The Renilla luciferase mRNA is engineered as a fusion mRNA with sequence elements present in the HBV genome, such that the fusion mRNA becomes a target for the NUC050 eiRNA plasmid, and the signal from Renilla is a measure of the gene silencing effect of NUC050. Activity of NUC050 will therefore result in a reduction of the Renilla luciferase signal even though it targets HBV sequences because the HBV sequences are present at the end of the Renilla mRNA. The FF luciferase signal serves as a normalization standard to correct for overall variability in target plasmid delivery/transfection, because it is not subject to down modulation by the eiRNA effector, but is dependent on the same plasmid for expression. Thus, taking the ratio, JF:FF luciferase normalizes for the liver-directed expression of plasmid. In cases where an insufficient FF luciferase is observed, it can be concluded that the plasmid was not delivered, and therefore the sample is not valid for analysis.

In vivo subcutaneous delivery of eiRNA: dual luciferase model

C57Bl/6 female mice were given a subcutaneous (SC) injection of either NUC 050 (drug eiRNA substance) or NUC 049 (negative control eiRNA substance) formulation at a volume of 200 μl, concentration of 1.5 mg/ml. The formulations consisted of DNA in an isotonic saline solution. Six days after dosing, all mice were given a hydrodynamic injection (HDI), or "challenge," of 1 ug of the expression plasmid (NUC 060, dual-luciferase HBV-fusion plasmid). HDI is a mechanism that allows selective transfection of liver hepatocytes.

Five days after the hydrodynamic injection (day 11), all mice were sacrificed and their livers were dissected, frozen, and stored at −70 C. Livers were homogenized with a mechanical homogenizer in a cell lysis buffer, centrifuged, and the supernatant was removed for analysis. Supernatant samples from all livers were assayed for the presence of both Renilla and Firefly luciferase proteins. The ratio of Renilla:Firefly luciferase (RLU) represents a normalized expression profile and serves as the output measure of the assay. The mean Renilla:Firefly luciferase ratio of the NUC 050 group is compared to the mean ratio of the NUC 049 group. This difference is represented as a net ratio value and a percent difference:

$$\% \text{ Difference} = \frac{\text{Mean } NUC\ 050 - \text{Mean } NUC\ 049}{\text{Mean } NUC\ 049} \times 100\%$$

The difference of the two means is tested for statistical significance using a nonparametric 2-sample Wilcoxon test for a p-value less than 0.05.

Figure 8:
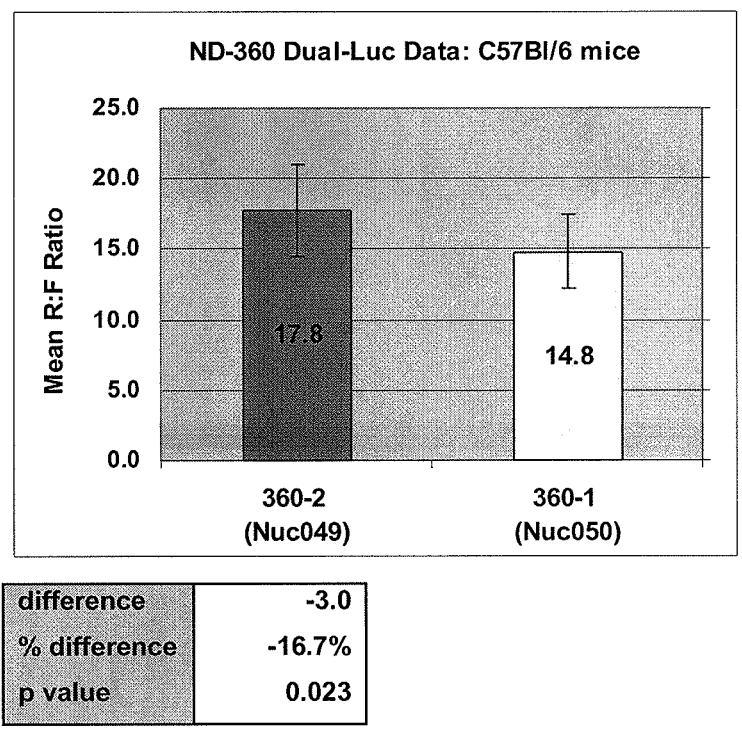
FIG. 8. Graph showing the ND-360 ratio of Renilla:Firefly luciferase (RLU) in response to subcutaneous delivery/administration of NUC050 versus NUC049 in C57Bl/6 mice. Mice were administered either NUC050 plasmid or negative control plasmid NUC049 via subcutaneous (SC) injection at day 0. Both groups of mice received a hydrodynamic injection (HDI) of the dual-luciferase reporter plasmid NUC060 at day 6. Values represent the mean Renilla RLU/Firefly RLU ratio in the liver for each group of animals on day 11. The 16.7% difference is statistically significant by nonparametric Wilcoxon two-sample test ($p<0.05$).

In this experiment, 15 animals were used for each treatment group. Levels of FF luciferase were acceptable for 8/15 animals in both the eiRNA (NUC050) group and the control (NUC049) group. A box-and-whisker plot of Renilla:FF activity ratios in liver cells shows a clear and statistically significant decrease of the Renilla Luciferase-HBV mRNA fusion target in the treatment vs. the control group. Mean levels of the target mRNA are reduced by 16.7% in the treatment group (see FIGS. 8 and 9, Tables 6 & 7).

The observed silencing of the target mRNA indicates that either the plasmid DNA, the expressed eiRNA and/or its processed product (ie. the ds siRNA or RNA charged RNA Induced Silencing Complex) have been transported from the subcutaneous injection site to hepatocytes in the liver. This transport may be mediated by cells at the injection site. Regardless of the mechanism involved however, these results show that subcutaneous injection of an eiRNA expressing plasmid can reduce the levels of target mRNA at a distal site, in this case liver hepatocytes.

TABLE 6

Individual Mouse Values (ratios)

|   | 360-1 (Nuc050) | 360-2 (Nuc049) |
|---|---|---|
| 1 | 12.0 | 12.3 |
| 2 | 12.2 | 14.4 |
| 3 | 12.3 | 17.6 |
| 4 | 13.3 | 17.7 |
| 5 | 16.1 | 18.2 |
| 6 | 16.9 | 18.3 |
| 7 | 17.2 | 21.8 |
| 8 | 18.5 | 22.1 |
| Mean | 14.8 | 17.8 |
| Sd | 2.6 | 3.3 |

TABLE 7

Additional Analysis

|   | 360-1 (Nuc050) | 360-2 (Nuc049) |
|---|---|---|
| Mean | 14.81 | 17.79 |
| Standard Error | 0.93 | 1.17 |
| Median | 14.68 | 17.94 |
| Mode | #N/A | #N/A |
| Standard Deviation | 2.62 | 3.30 |
| Sample Variance | 6.88 | 10.88 |
| Kurtosis | −2.10 | −0.18 |
| Skewness | 0.17 | −0.34 |
| Range | 6.47 | 9.78 |
| Minimum | 12.03 | 12.28 |
| Maximum | 18.50 | 22.06 |
| Sum | 118.47 | 142.30 |
| Count | 8 | 8 |

Example 10

Therapeutic Inhibition of HBV sAg Gene Expression In Vivo by Subcutaneous Adoptive Transfer of NUC050-Transfected Cells The NUC050 vector encodes four different shRNA molecules which target various portions of the hepatitis B genome for degradation via the cellular RNAi mechanism. Three of these target the HBsAg regions contained in the target vector preadministered to the mice.

In the therapeutic model, animals receive exogenous RNA target in the form of a plasmid expressing the surface antigen coding sequence of HBV via hydrodynamic tail vein injection. Hydrodynamic injection is a method using a large volume with rapid injection time, to preferentially direct the DNA plasmid to the liver where it is expressed.

To obtain mice expressing a target gene in liver, HBsAg (surface antigen) cDNA was placed under the control of a liver-specific promoter in a commercially available plasmid vector (pLIVE). On Day −7, this vector was injected hydrodynamically into an immunodeficient strain of mice (NOD.CB17-Pkrdc$^{scid}$/J). In this way, DNA is largely localized to liver hepatocytes and the tissue-specific promoter further restricts expression of the sAg mRNA to these cells. Since the mice are immunodeficient, they are able to express the target gene for long periods of time (greater than a month) because immune response to the foreign protein encoded by the target gene will not be made.

Four days following target plasmid administration (Day −3), the mice were bled to determine levels of circulating HBsAg in serum. On Day 0, mice were subcutaneously injected with a suspension of RD (rhabdomyosarcoma) cells (RD; ATCC CCL-135) which had been transfected with NUC050 within a total volume of 0.2-0.4 ml. A control group of mice was treated similarly with a suspension of RD cells which had been transfected with the negative control NUC049 plasmid.

The NUC050 and NUC049 cell suspensions were prepared identically as follows: Briefly, RD cells were plated in T150 flasks (150 cm$^2$) at a density of 5×10$^6$ cells per flask and incubated@37° C., 5% CO$_2$. One day later they were transfected with either NUC050 vector or NUC049 negative control vector (28 ug/flask, respectively) mixed with the Roche Fugene™ 6 transfection reagent (cat. #11814443001). Cells were roughly 65% confluent at the time of transfection. After transfection mix was added, the RD cells were incubated overnight@37° C., 5% CO$_2$. The next day the cells were rinsed in 1× Dulbecco's Phosphate Buffered Saline (DPBS) and the medium was changed to fresh Dulbecco's Modified Eagle's Medium (DMEM) with 10% FBS. Three days post transfection, RD cells were rinsed in sterile DPBS and trypsinized to liberate them from the flask surface. Cells were counted and multiple aliquots of 1×10$^8$ cells were rinsed twice in sterile DPBS and pelleted by centrifugation. The RD cells were then resuspended in 4.5 ml sterile DPBS. A 0.2-0.4 ml cell suspension containing approximately 8×10$^6$ cells was then injected subcutaneously into each NOD.CB17-Prkdc$^{scid}$/J (NOD/SCID) mouse in the right flank, using a 23 gauge needle.

Animals were subsequently bled again on Days 6 and 11 post eiRNA vector administration, respectively and levels of serum HBsAg were determined using a commercially available HBsAg ELISA (Bio-Rad, Hercules, Calif. HBsAg 3.0 EIA cat#. 32591). Animals are scheduled to be bled again on Days 18 and 25 days post eiRNA vector administration as well with subsequent HBsAg level measurement. From 9 to 11 mice were used for each treatment group and the results are presented as HBsAg percent of initial HBsAg values (pretreatment). The ability of the adoptively transferred NUC050 vector treated cells to decrease HBsAg expression was estimated by calculating, for each bleed day, a normalized difference value of average HBsAg levels for control minus experimental groups. Normalization was done by calculating the percent of HBsAg for each subsequent bleed day, relative to the HBsAg values on pretreatment.

Day 6 and Day 11 show difference averages of −8% and −18% respectively, between NUC050 and NUC049 (FIG. 10 and Table 8). (These values reflect underlying normalized average values of 124% and 132% prebleed (pretreatment) values for NUC050 and NUC049 respectively for Day 6. The normalized average values compared to Prebleed values were 105% (NUC050) vs. 123% (NUC049) for Day 11). Based on this trend and historical data trends within this animal model, we anticipate increasing differences between treatment and control groups in the subsequent time points (Day 18 and Day 25).

Exogenously transfected cells e.g. muscle cells as described herein could also be cultured and their culture medium used as a source of RNA-containing "blebs" or exovesicles for use as described elsewhere herein. One of skill in the art will also recognize that the methods described can be utilized for heterologous or autologous transplant into a recipient mammal of exogenously transfected cells such as muscle cells for use as a source of biologically active RNA effector molecules delivered to distal cells including liver cells such as hepatocytes.

TABLE 8

Normalized HBsAg Levels (% prebleed)

| time pt | Nuc049 | Nuc050 | Difference |
|---------|--------|--------|------------|
| Day 6   | 132.2  | 123.8  | −8.4       |
| Day 11  | 123.0  | 105.4  | −17.6      |

Example 11

In Vivo Electroporation Delivery of eiRNA Against Endogenous Interleukin-12 (IL-12)

In this experiment, immunocompetent BALB/cJ mice are administered an anti-IL-12 eiRNA vector or an irrelevant, negative control eiRNA vector via intramuscular (IM) injection concomitantly with electroporation (EP), (IM-EP). The anti-IL-12 eiRNA plasmid vector encodes a shRNA molecule driven by a 7SK promoter, which targets the p40 subunit of the mouse IL-12 mRNA sequence for degradation via the sequence specific cellular RNAi mechanism. Following IM-EP administration, shRNA molecules encoded by the eiRNA vectors are transcribed to high copy levels in the electroporated muscle (2,000,000,000 copies of individual shRNA detectable by QRT-PCR in piece of electroporated muscle).

One day, four days, seven days, and 11 days following dosing with the anti-IL-12 and control eiRNA vectors, blood is collected from mice for measurement of IL-12 using a commercially-available ELISA (R&D Systems). If IM-EP delivery of the anti-IL-12 eiRNA vector is specifically able to downregulate endogenous serum IL-12 (as compared to the control vector), then transfected muscle must be able to relay plasmid expressed molecules such as shRNA/siRNA produced in the muscle to at least some of the various distal immune cells (macrophages, monocytes, dendritic cells, and B cells) which express IL-12 and where RNAi of the IL-12 target mRNA occurs. Because IL-12 is expressed by multiple cell types throughout the body, significant downregulation would be likely to signal substantial delivery to multiple sites where such cells reside. In our described study, we expect intramuscular injection of the anti-IL-12 eiRNA vector with electroporation (IM-EP) in mice to result in sustained downregulation of endogenous serum IL-12 over all time points. We expect that alternative methods of delivery to muscle cells (e.g., vascular delivery with increased pressure to mammalian limb muscle as described elsewhere herein) would also achieve downregulation of a target nucleic acid such as IL-12 in distal non-muscle cells including immune cells.

All publications, patents and patent applications discussed herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed:

1. A method of delivering at least one RNA to liver or liver tissue in an animal comprising:
    transfecting at least one muscle or skin cell of said animal with a double-stranded RNA (dsRNA) or with a nucleic acid encoding said RNA, wherein said transfection results in said RNA being delivered to at least one cell in the liver or liver tissue, wherein one strand of said dsRNA is substantially complementary to a region of RNA produced by a pathogen infecting the liver or liver tissue.

2. The method of claim 1 wherein the pathogen is a virus.

3. The method of claim 2 wherein the virus is a Hepatitis virus.

4. The method of claim 1 wherein the muscle or skin cell is selected from the group consisting of fibroblast cells, cells in a dermal layer in the skin, cells in a subcutaneous layer of the skin, myocytes and myoblasts.

5. The method of claim 1 wherein the nucleic acid encoding said RNA is a DNA.

6. The method of claim 1 wherein the transfecting of the muscle cell is comprised of administering intramuscularly the dsRNA or nucleic acid encoding the RNA.

7. The method of claim 1 wherein the transfecting of the skin cell is comprised of administering subcutaneously or intradermally the dsRNA or nucleic acid encoding the RNA.

8. The method claim 1 wherein one strand of said dsRNA is substantially complementary to a region of a messenger RNA transcribed by a target gene of the pathogen infecting the liver or liver.

9. The method of claim 8 wherein the pathogen is a virus.

10. The method of claim 9 wherein the virus is Hepatitis virus.

11. The method of claim 10 wherein the hepatitis virus is a hepatitis B virus.

12. The method of claim 1 wherein said transfection is facilitated by one or more agents selected from the group consisting of polymer or peptide complexes, cationic amphiphiles, cationic lipids, cationic liposome formulations, a local anaesthetic, bupivacaine, particulates, gold particles, gene gun delivery, polycationic agents, cationic agents, spermine, spermine derivatives, spermidine, spermidine derivatives, cholesteryl spermine compounds, cholesteryl spermine carbamates, an electroporation-facilitating agent, poly-L-glutamate, electroporation, needle injection, needleless injection, and transdermal patch.

13. The method of claim 1 wherein said transfected cells further express a transmembrane or surface ligand specific for a receptor on the liver or liver tissue.

14. The method of claim 13 wherein a nucleic acid expressing said transmembrane or surface ligand is co-transfected with said nucleic acid encoding said dsRNA.

15. The method of claim 14 wherein said nucleic acid expressing said transmembrane or surface ligand and said nucleic acid encoding said dsRNA are encoded on a single vector or plasmid.

16. The method of claim 1 wherein said dsRNA is an shRNA or an siRNA having between 15 to about 50 base pairs.

17. The method of claim 1 wherein said transfection of said dsRNA to said muscle or skin cell does not trigger a detectable PKR response.

* * * * *

UNITED STATES PATENT AND TRADEMARK OFFICE
CERTIFICATE OF CORRECTION

PATENT NO. : 8,524,679 B2
APPLICATION NO. : 12/514237
DATED : September 3, 2013
INVENTOR(S) : Catherine Pachuk It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1092 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 10

<210> SEQ ID NO 1
<211> LENGTH: 21
<212> TYPE: RNA
<213> ORGANISM: Hepatitis B virus

<400> SEQUENCE: 1
ggauucagcg ccgacgggac g        21

<210> SEQ ID NO 2
<211> LENGTH: 44
<212> TYPE: DNA
<213> ORGANISM: Hepatitis B virus

<400> SEQUENCE: 2
ctcaactggt gtcgtggagt cggcaattca gttgagcgtc ccgt        44

<210> SEQ ID NO 3
<211> LENGTH: 57
<212> TYPE: DNA
<213> ORGANISM: Hepatitis B virus

<400> SEQUENCE: 3
ctcaactggt gtcgtggagt cggcaattca gttgagcgtc ccgtcggcgc tgaatcc        57

```
<210> SEQ ID NO 4
<211> LENGTH: 24
<212> TYPE: DNA
<213> ORGANISM: Hepatitis B virus

<400> SEQUENCE: 4
cagctgggag gattcagcgc cgac                                           24

<210> SEQ ID NO 5
<211> LENGTH: 57
<212> TYPE: DNA
<213> ORGANISM: Hepatitis B virus

<400> SEQUENCE: 5
ctcaactggt gtcgtggagt cggcaattca gttgagcgtc ccgtcggcgc tgaatcc      57

<210> SEQ ID NO 6
<211> LENGTH: 66
<212> TYPE: DNA
<213> ORGANISM: Hepatitis B virus

<400> SEQUENCE: 6
cagctgggag gattcagcgc cgacgggacg ctcaactgaa ttgccgactc cacgacacca   60
gttgag                                                              66

<210> SEQ ID NO 7
<211> LENGTH: 24
<212> TYPE: DNA
<213> ORGANISM: Hepatitis B virus

<400> SEQUENCE: 7
cagctgggag gattcagcgc cgac                                           24

<210> SEQ ID NO 8
<211> LENGTH: 66
<212> TYPE: DNA
<213> ORGANISM: Hepatitis B virus

<400> SEQUENCE: 8
cagctgggag gattcagcgc cgacgggacg ctcaactgaa ttgccgactc cacgacacca   60
gttgag                                                              66

<210> SEQ ID NO 9
<211> LENGTH: 18
<212> TYPE: DNA
<213> ORGANISM: Hepatitis B virus

<400> SEQUENCE: 9
tgccctgcga gttgactt                                                  18

<210> SEQ ID NO 10
<211> LENGTH: 20
<212> TYPE: DNA
<213> ORGANISM: Hepatitis B virus

<400> SEQUENCE: 10
tcaactggtg tcgtggagtc                                                20
```